Figure 1A:
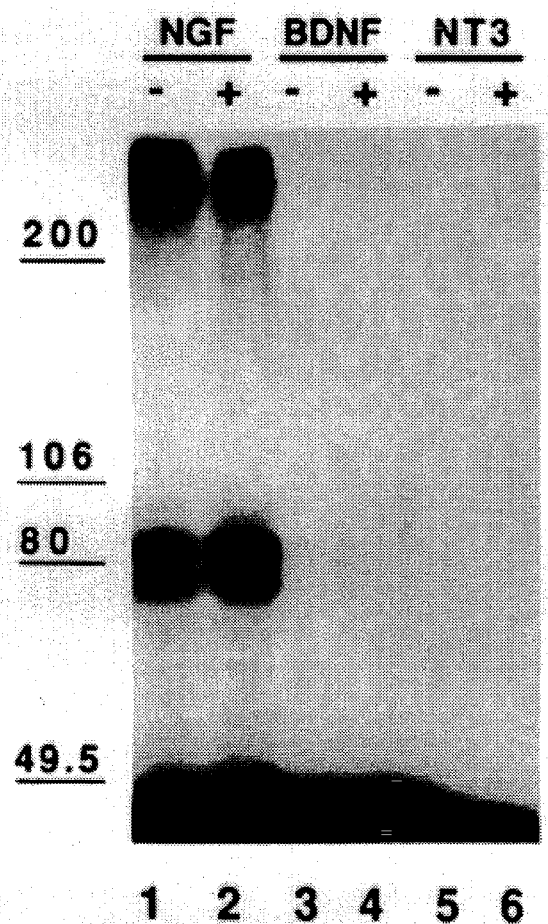

United States Patent [19]
Squinto et al.

[11] Patent Number: 5,622,862
[45] Date of Patent: Apr. 22, 1997

[54] ASSAY SYSTEMS FOR TRKB NEUROTROPHIN ACTIVITY

[75] Inventors: Stephen P. Squinto, Irvington; David Glass; Thomas H. Aldrich, both of New York; Peter DiStefano, Carmel; Trevor Stitt, Huntington Station; Mark E. Furth, Pelham; George D. Yancopoulos, Briarcliff Manor, all of N.Y.

[73] Assignee: Regeneron Pharmaceuticals, Inc., Tarrytown, N.Y.

[21] Appl. No.: 339,578

[22] Filed: Nov. 14, 1994

Related U.S. Application Data

[63] Continuation of Ser. No. 690,199, Apr. 23, 1991, abandoned.
[51] Int. Cl.⁶ .............................. C12N 15/00; C12N 5/10
[52] U.S. Cl. ...................... 435/353; 435/7.21; 435/325; 536/23.5
[58] Field of Search ..................... 536/23.5; 435/69.1, 435/7.21, 240.2, 320.1

[56] References Cited

U.S. PATENT DOCUMENTS

| | | | |
|---|---|---|---|
| 4,963,481 | 10/1990 | deVilliers | 435/69.1 |
| 5,231,001 | 7/1993 | Kaplan et al. | 435/7.21 |
| 5,348,856 | 9/1994 | Barbacid | 435/6 |

OTHER PUBLICATIONS

Klein, R. et al., *Cell*, 65:189–197, 1991. (Klein et al. (IV)).
Klein, R. et al., *Development*, 109:845–850, 1990. (Klein et al. (II)).
Klein R. et al., *Cell*, 61:647–656, 1990. (Klein et al. (III)).
Klein, R. et al., *EMBO J.*, 8(12): 3701–09, 1989.
Covlier, F. et al., *Mol. Cell. Biol.*, 10(8): 4202–4210, 1990.
Martin–Zanca, D. et al., Mol. Cell. Biol., 9(1):24–33, 1989, (I).
Oskam, R. et al., *PNAS*, 85: 2964–68, 1988.
Mitra, G. et al., *PNAS*, 84: 6707–6711, 1987.
Kozma, S. et al., *EMBO J.*, 7 (1): 147–154, 1988.
Bongarzone, I. et al., *Oncogene*, 4(12): 1457–62, 1989.
Martin–Zanca, D. et al., *Genes & Development*, 4: 683–94, 1990 (II).
Zhan, X. et al., *Mol. Cell. Biol.*, 6(10): 3541–44, 1986.
Selden, R. et al. *Mol. Cell. Biol.*, 6(9): 3173–3179, 1986.
Greene, L. et al., *PNAS*, 73(7): 2424–28, 1976.
Greenberg, M. et al., *J. Biol. Chem.*, 260 (26): 14101–110, 1985.
Gilman, M. et al., *Mol. Cell. Biol.*, 6(12): 4305–16, 1986.
Fields, B. (ed.) et al., *Fundamental Virology*, 2nd Edition, Raven Press, NY, 1990, pp. 935–937.

*Primary Examiner*—Marianne P. Allen
*Attorney, Agent, or Firm*—Gail M. Kempler

[57] ABSTRACT

The present invention provides for assay systems that may be used to detect and/or measure neurotrophin activity or to identify agents that exhibit neurotrophin-like activity, and for methods of using such assay systems. It is based, at least in part, on the discovery that the trkB protooncogene encodes a tyrosine kinase receptor that may serve as a functional binding protein for BDNF and NT-3. Such assay systems may be of particular value in identifying new neurotrophins or agents with neurotrophin-like activity. In various embodiments, the assay systems and methods of the invention may be used to detect and/or measure the binding of neurotrophin to trkB, either using direct binding studies or the detection of the secondary affects of trkB/neurotrophin binding. The present invention also has diagnostic and therapeutic utilities. In particular embodiments of the invention, methods of detecting aberrancies in trkB function or expression may be used in the diagnosis of neurological disorders. In other embodiments, manipulation of the trkB/neurotrophin interaction may be used in the treatment of neurological disorders, including Alzheimer's disease, Parkinson's disease, and amyotrophic lateral sclerosis (Lou Gehrig's disease).

1 Claim, 18 Drawing Sheets

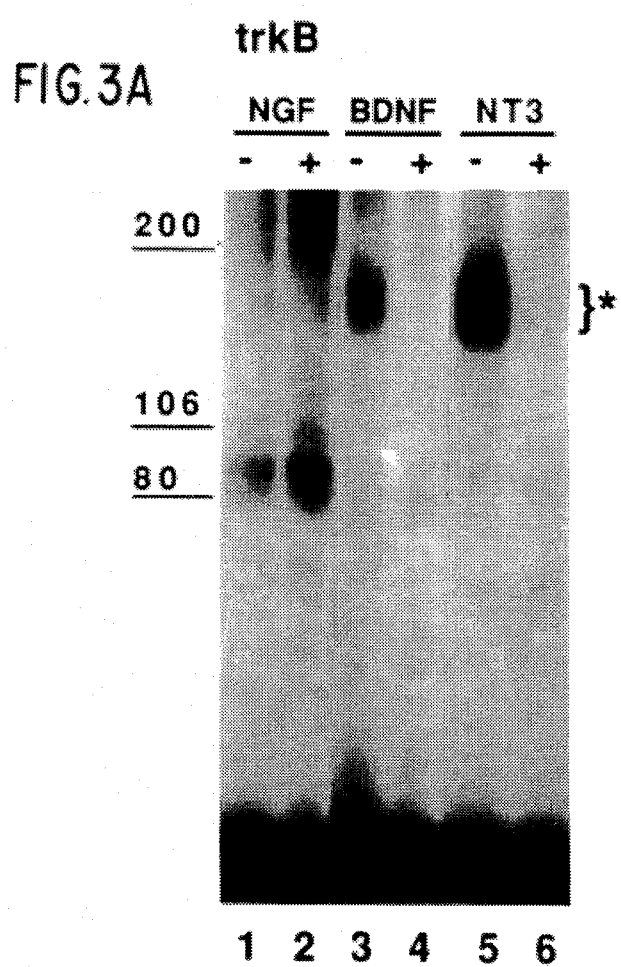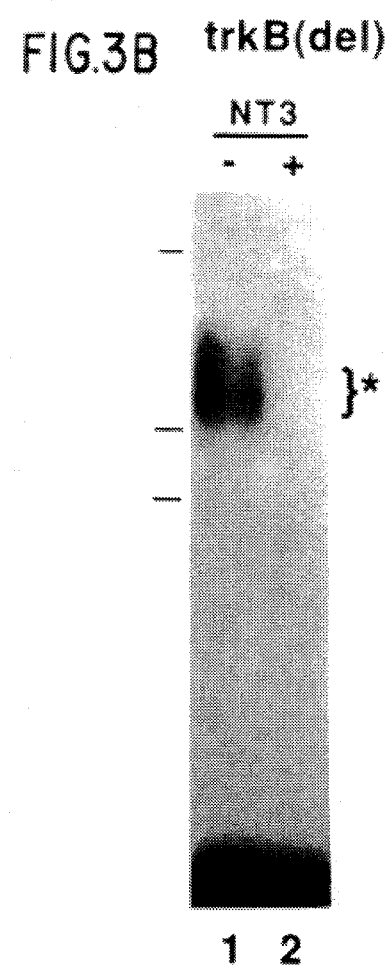

T24-ras + BSA
(6500)

trk B + NGF
(ND)

trk B + BSA
(0)

trk B + NT-3
(1200)

trk B + BDNF
(8700)

FIG. 8A

| | | | | | | | | | | | | | | | | |
|---|---|---|---|---|---|---|---|---|---|---|---|---|---|---|---|---|
| ATG | TCG | CCC | TGG | CTG | AAG | TGG | CAT | GGA | CCC | GCC | ATG | GCG | CGG | CTC | TGG | 48 |
| Met | Ser | Pro | Trp | Leu | Lys | Trp | His | Gly | Pro | Ala | Met | Ala | Arg | Leu | Trp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GGC | TTA | TGC | CTG | CTG | GTC | TTG | GGC | TTC | TGG | AGG | GCC | TCT | CTC | GCC | TGC | 96 |
| Gly | Leu | Cys | Leu | Leu | Val | Leu | Gly | Phe | Trp | Arg | Ala | Ser | Leu | Ala | Cys | |
| | | | 20 | | | | | 25 | | | | | 30 | | | |

| | | | | | | | | | | | | | | | | |
|---|---|---|---|---|---|---|---|---|---|---|---|---|---|---|---|---|
| CCG | ACG | TCC | TGC | AAA | TGC | AGT | TCC | GCT | AGG | ATT | TGG | TGT | ACT | GAG | CCT | 144 |
| Pro | Thr | Ser | Cys | Lys | Cys | Ser | Ser | Ala | Arg | Ile | Trp | Cys | Thr | Glu | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| TCT | CCA | GGC | ATC | GTG | GCA | TTC | CCG | AGG | TTG | GAA | CCT | AAC | AGC | GTT | GAC | 192 |
| Ser | Pro | Gly | Ile | Val | Ala | Phe | Pro | Arg | Leu | Glu | Pro | Asn | Ser | Val | Asp | |
| | | 50 | | | | | 55 | | | | | 60 | | | | |

| | | | | | | | | | | | | | | | | |
|---|---|---|---|---|---|---|---|---|---|---|---|---|---|---|---|---|
| CCG | GAG | AAC | ATC | ACG | GAA | ATT | CTC | ATT | GCA | AAC | CAG | AAA | AGG | CTA | GAA | 240 |
| Pro | Glu | Asn | Ile | Thr | Glu | Ile | Leu | Ile | Ala | Asn | Gln | Lys | Arg | Leu | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATC | ATC | AAT | GAA | GAT | GAC | GTT | GAA | GCT | TAC | GTG | GGG | CTG | AGA | AAC | CTT | 288 |
| Ile | Ile | Asn | Glu | Asp | Asp | Val | Glu | Ala | Tyr | Val | Gly | Leu | Arg | Asn | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ACA | ATT | GTG | GAT | TCC | GGC | TTA | AAG | TTT | GTG | GCT | TAC | AAA | GCG | TTT | CTG | 336 |
| Thr | Ile | Val | Asp | Ser | Gly | Leu | Lys | Phe | Val | Ala | Tyr | Lys | Ala | Phe | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| AAA | AAC | AGC | AAC | CTG | CGG | CAC | ATA | AAT | TTC | ACA | CGA | AAC | AAG | CTG | ACG | 384 |
| Lys | Asn | Ser | Asn | Leu | Arg | His | Ile | Asn | Phe | Thr | Arg | Asn | Lys | Leu | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| AGT | TTG | TCC | AGG | AGA | CAT | TTC | CGC | CAC | CTT | GAC | TTG | TCT | GAC | CTG | ATC | 432 |
| Ser | Leu | Ser | Arg | Arg | His | Phe | Arg | His | Leu | Asp | Leu | Ser | Asp | Leu | Ile | |
| | | 130 | | | | | 135 | | | | | 140 | | | | |

| | | | | | | | | | | | | | | | | |
|---|---|---|---|---|---|---|---|---|---|---|---|---|---|---|---|---|
| CTG | ACG | GGT | AAT | CCG | TTC | ACG | TGC | TCC | TGC | GAC | ATC | ATG | TGG | CTC | AAG | 480 |
| Leu | Thr | Gly | Asn | Pro | Phe | Thr | Cys | Ser | Cys | Asp | Ile | Met | Trp | Leu | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ACT | CTC | CAG | GAG | ACT | AAA | TCC | AGC | CCC | GAC | ACT | CAG | GAT | TTG | TAC | TGC | 528 |
| Thr | Leu | Gln | Glu | Thr | Lys | Ser | Ser | Pro | Asp | Thr | Gln | Asp | Leu | Tyr | Cys | |
| | | | | 165 | | | | | 170 | | | | | 175 | | |

| | | | | | | | | | | | | | | | | |
|---|---|---|---|---|---|---|---|---|---|---|---|---|---|---|---|---|
| CTC | AAT | GAG | AGC | AGC | AAG | AAC | ATG | CCC | CTG | GCG | AAC | CTG | CAG | ATA | CCC | 576 |
| Leu | Asn | Glu | Ser | Ser | Lys | Asn | Met | Pro | Leu | Ala | Asn | Leu | Gln | Ile | Pro | |
| | | | | 180 | | | | | 185 | | | | | 190 | | |

| | | | | | | | | | | | | | | | | |
|---|---|---|---|---|---|---|---|---|---|---|---|---|---|---|---|---|
| AAT | TGT | GGT | CTG | CCA | TCT | GCA | CGT | CTG | GCT | GCT | CCT | AAC | CTC | ACC | GTG | 624 |
| Asn | Cys | Gly | Leu | Pro | Ser | Ala | Arg | Leu | Ala | Ala | Pro | Asn | Leu | Thr | Val | |
| | | 195 | | | | | 200 | | | | | 205 | | | | |

FIG. 8B

| | |
|---|---|
| GAG GAA GGA AAG TCT GTG ACC CTT TCC TGC AGT GTG GGG GGT GAC CCA<br>Glu Glu Gly Lys Ser Val Thr Leu Ser Cys Ser Val Gly Gly Asp Pro<br>    210                215                220 | 672 |
| CTC CCC ACC TTG TAC TGG GAC GTT GGG AAT TTG GTT TCC AAG CAC ATG<br>Leu Pro Thr Leu Tyr Trp Asp Val Gly Asn Leu Val Ser Lys His Met<br>225                230                235                240 | 720 |
| AAT GAA ACA AGC CAC ACA CAG GGC TCC TTA AGG ATA ACG AAC ATT TCA<br>Asn Glu Thr Ser His Thr Gln Gly Ser Leu Arg Ile Thr Asn Ile Ser<br>                245                250                255 | 768 |
| TCT GAT GAC AGT GGA AAG CAA ATC TCT TGT GTG GCA GAA AAC CTT GTA<br>Ser Asp Asp Ser Gly Lys Gln Ile Ser Cys Val Ala Glu Asn Leu Val<br>            260                265                270 | 816 |
| GGA GAA GAT CAA GAT TCT GTG AAC CTC ACT GTG CAT TTT GCG CCA ACT<br>Gly Glu Asp Gln Asp Ser Val Asn Leu Thr Val His Phe Ala Pro Thr<br>        275                280                285 | 864 |
| ATC ACG TTT CTC GAG TCT CCA ACC TCA GAT CAC CAC TGG TGC ATT CCA<br>Ile Thr Phe Leu Glu Ser Pro Thr Ser Asp His His Trp Cys Ile Pro<br>        290                295                300 | 912 |
| TTC ACT GTG AGA GGC AAC CCC AAG CCT GCG CTT CAG TGG TTC TAC AAT<br>Phe Thr Val Arg Gly Asn Pro Lys Pro Ala Leu Gln Trp Phe Tyr Asn<br>305                310                315                320 | 960 |
| GGG GCC ATA CTG AAT GAG TCC AAG TAC ATC TGT ACT AAG ATC CAC GTC<br>Gly Ala Ile Leu Asn Glu Ser Lys Tyr Ile Cys Thr Lys Ile His Val<br>                325                330                335 | 1008 |
| ACC AAT CAC ACG GAG TAC CAT GGC TGC CTC CAG CTG GAT AAC CCC ACT<br>Thr Asn His Thr Glu Tyr His Gly Cys Leu Gln Leu Asp Asn Pro Thr<br>            340                345                350 | 1056 |
| CAT ATG AAT AAC GGA GAC TAC ACC CTG ATG GCC AAG AAC GAG TAT GGG<br>His Met Asn Asn Gly Asp Tyr Thr Leu Met Ala Lys Asn Glu Tyr Gly<br>                355                360                365 | 1104 |
| AAG GAT GAG AGA CAG ATC TCC GCT CAC TTC ATG GGC CGG CCT GGA GTC<br>Lys Asp Glu Arg Gln Ile Ser Ala His Phe Met Gly Arg Pro Gly Val<br>    370                375                380 | 1152 |
| GAC TAC GAG ACA AAC CCA AAT TAC CCT GAA GTC CTC TAT GAA GAC TGG<br>Asp Tyr Glu Thr Asn Pro Asn Tyr Pro Glu Val Leu Tyr Glu Asp Trp<br>385                390                395                400 | 1200 |
| ACC ACG CCA ACT GAC ATT GGG GAT ACT ACG AAC AAA AGT AAT GAA ATC<br>Thr Thr Pro Thr Asp Ile Gly Asp Thr Thr Asn Lys Ser Asn Glu Ile<br>                405                410                415 | 1248 |

FIG. 8C

| | |
|---|---|
| CCC TCC ACG GAT GTT GCT GAC CAA AGC AAT CGG GAG CAT CTC TCG GTC<br>Pro Ser Thr Asp Val Ala Asp Gln Ser Asn Arg Glu His Leu Ser Val<br>            420                          425                         430 | 1296 |
| TAT GCC GTG GTG GTG ATT GCA TCT GTG GTG GGA TTC TGC CTG CTG GTG<br>Tyr Ala Val Val Val Ile Ala Ser Val Val Gly Phe Cys Leu Leu Val<br>            435                          440                         445 | 1344 |
| ATG TTG CTC CTG CTC AAG TTG GCG AGA CAT TCC AAG TTT GGC ATG AAA<br>Met Leu Leu Leu Leu Lys Leu Ala Arg His Ser Lys Phe Gly Met Lys<br>            450                          455                         460 | 1392 |
| GGC CCA GCT TCG GTC ATC AGC AAC GAC GAT GAC TCT GCC AGC CCC CTC<br>Gly Pro Ala Ser Val Ile Ser Asn Asp Asp Asp Ser Ala Ser Pro Leu<br>465                        470                        475                         480 | 1440 |
| CAC CAC ATC TCC AAT GGG AGT AAC ACT CCA TCT TCT TCG GAG GGC GGT<br>His His Ile Ser Asn Gly Ser Asn Thr Pro Ser Ser Ser Glu Gly Gly<br>                       485                          490                         495 | 1488 |
| CCC GAC GCT GTC ATT ATT GGA ATG ACC AAG ATT CCT GTT ATT GAA AAC<br>Pro Asp Ala Val Ile Ile Gly Met Thr Lys Ile Pro Val Ile Glu Asn<br>                  500                          505                         510 | 1536 |
| CCC CAG TAC TTT GGC ATC ACC AAC AGT CAG CTC AAG CCA GAC ACA TTT<br>Pro Gln Tyr Phe Gly Ile Thr Asn Ser Gln Leu Lys Pro Asp Thr Phe<br>            515                          520                         525 | 1584 |
| GTT CAG CAC ATC AAG AGA CAC AAC ATC GTT CTG AAG AGG GAA CTT GGG<br>Val Gln His Ile Lys Arg His Asn Ile Val Leu Lys Arg Glu Leu Gly<br>         530                          535                         540 | 1632 |
| GAA GGA GCC TTC GGG AAA GTT TTC CTT GCC GAG TGC TAC AAC CTC TGC<br>Glu Gly Ala Phe Gly Lys Val Phe Leu Ala Glu Cys Tyr Asn Leu Cys<br>545                        550                        555                         560 | 1680 |
| CCA GAG CAG GAT AAG ATC CTG GTG GCT GTG AAG ACG CTG AAG GAC GCC<br>Pro Glu Gln Asp Lys Ile Leu Val Ala Val Lys Thr Leu Lys Asp Ala<br>                  565                          570                         575 | 1728 |
| AGC GAC AAT GCA CGC AAG GAC TTT CAT CGG GAA GCT GAG CTG CTG ACC<br>Ser Asp Asn Ala Arg Lys Asp Phe His Arg Glu Ala Glu Leu Leu Thr<br>            580                          585                         590 | 1776 |
| AAC CTC CAG CAC GAG CAC ATT GTC AAG TTC TAC GGT GTC TGT GTG GAG<br>Asn Leu Gln His Glu His Ile Val Lys Phe Tyr Gly Val Cys Val Glu<br>         595                          600                         605 | 1824 |
| GGC GAC CCA CTC ATC ATG GTC TTT GAG TAC ATG AAG CAC GGG GAC CTC<br>Gly Asp Pro Leu Ile Met Val Phe Glu Tyr Met Lys His Gly Asp Leu<br>            610                          615                         620 | 1872 |

FIG. 8D

```
AAC AAG TTC CTT AGG GCA CAC GGG CCC GAC GCA GTG CTG ATG GCA GAG      1920
Asn Lys Phe Leu Arg Ala His Gly Pro Asp Ala Val Leu Met Ala Glu
625                 630                 635                 640

GGT AAC CCG CCC ACA GAG CTG ACG CAG TCG CAG ATG CTG CAC ATC GCT      1968
Gly Asn Pro Pro Thr Glu Leu Thr Gln Ser Gln Met Leu His Ile Ala
                645                 650                 655

CAG CAA ATC GCA GCA GGT ATG GTC TAC CTG GCG TCC CAA CAC TTT GTG      2016
Gln Gln Ile Ala Ala Gly Met Val Tyr Leu Ala Ser Gln His Phe Val
            660                 665                 670

CAC CGT GAC CTG GCC ACC CGG AAC TGC CTG GTG GGA GAG AAC CTG CTG      2064
His Arg Asp Leu Ala Thr Arg Asn Cys Leu Val Gly Glu Asn Leu Leu
        675                 680                 685

GTG AAA ATT GGG GAC TTT GGG ATG TCC CGA GAT GTG TAC AGC ACC GAC      2112
Val Lys Ile Gly Asp Phe Gly Met Ser Arg Asp Val Tyr Ser Thr Asp
    690                 695                 700

TAC TAT CGG GTC GGT GGC CAC ACA ATG TTG CCC ATC CGA TGG ATG CCT      2160
Tyr Tyr Arg Val Gly Gly His Thr Met Leu Pro Ile Arg Trp Met Pro
705                 710                 715                 720

CCA GAG AGC ATC ATG TAT AGG AAA TTC ACC ACC GAG AGC GAC GTC TGG      2208
Pro Glu Ser Ile Met Tyr Arg Lys Phe Thr Thr Glu Ser Asp Val Trp
                725                 730                 735

AGC CTG GGC GTT GTG TTG TGG GAG ATC TTC ACC TAC GGC AAG CAG CCC      2256
Ser Leu Gly Val Val Leu Trp Glu Ile Phe Thr Tyr Gly Lys Gln Pro
            740                 745                 750

TGG TAT CAG CTA TCG AAC AAT GAG GTG ATA GAG TGC ATC ACC CAG GGA      2304
Trp Tyr Gln Leu Ser Asn Asn Glu Val Ile Glu Cys Ile Thr Gln Gly
        755                 760                 765

AGA GTC CTT CAG CGG CCT CGA ACC TGT CCC CAG GAG GTG TAT GAG CTC      2352
Arg Val Leu Gln Arg Pro Arg Thr Cys Pro Gln Glu Val Tyr Glu Leu
    770                 775                 780

ATG CTC GGA TGC TGG CAG CGG GAA CCA CAC ACC CGG AAG AAC ATC AAG      2400
Met Leu Gly Cys Trp Gln Arg Glu Pro His Thr Arg Lys Asn Ile Lys
785                 790                 795                 800

AGC ATC CAC ACC CTC CTT CAG AAC TTG GCC AAG GCA TCT CCC GTC TAC      2448
Ser Ile His Thr Leu Leu Gln Asn Leu Ala Lys Ala Ser Pro Val Tyr
                805                 810                 815

CTG GAT ATC CTA GGC                                                  2463
Leu Asp Ile Leu Gly
            820
```

ASSAY SYSTEMS FOR TRKB NEUROTROPHIN ACTIVITY

This is a continuation of application Ser. No. 07/690,199 filed Apr. 23, 1991, now abandoned.

1. INTRODUCTION

The present invention provides for assay systems that may be used to detect and/or measure neurotrophin activity or to identify agents that exhibit neurotrophin-like activity. It is based, at least in part, on the discovery that the trkB proto-oncogene encodes a tyrosine kinase receptor that may serve as a functional binding protein for BDNF and NT-3. The present invention also provides for diagnostic and therapeutic methods based on the interaction between BDNF and/or NT-3 and trkB.

2. BACKGROUND OF THE INVENTION

The development and maintenance of the vertebrate nervous system depends on specific proteins, termed neurotrophic factors, originally defined by their ability to support the survival of neuronal populations (Snider and Johnson, 1989, Ann. Neurol. 26:489). Neurotrophic factors have also been implicated in processes involving the proliferation and differentiation of neurons (Cattaneo and McKay, 1990, Nature 347: 762–765; Lindsay and Harmar, 1989, Nature 337: 362–364), and they may play additional, thus far unexplored, roles both within as well as outside of the nervous system. Brain-derived neurotrophic factor (BDNF) and neurotrophin-3 (NT-3) have recently been molecularly cloned and shown to be structurally related to the prototypical neuronal survival molecule, nerve growth factor (NGF). (Leibrock et al., 1989, Nature 341:149–152; Hohn et al., 1990, Nature 344:339–341; Maisonpierre et al., 1990a, Science 247:1446–1451; Rosenthal et al., 1990, Neuron 4:767–773; Ernfors et al., 1990, Proc. Natl. Acad. Sci. U.S.A. 87:5454–5458; Jones and Reichardt, 1990, Proc. Natl. Acad. Sci. U.S.A. 87:8060–8064). These three related factors (designated "neurotrophins") do not display any structural homology to a fourth neurotrophic factor, ciliary neurotrophic factor (CNTF). (Lin et al., 1989, Science 246:1023–1025; Stockli et al., 1989, Nature 342:920–923).

The receptor and signal transduction pathways utilized by NGF have been extensively studied, in large part due to the availability of a pheochromocytoma cell line (PC12) which differentiates in response to NGF (Greene and Tischler, 1976, Proc. Natl. Acad. Sci. U.S.A. 73:2424). These studies have resulted in the cloning of a transmembrane protein (designated "LNGFR" for low-affinity NGF receptor) which binds NGF with relatively low affinity (Chao et al., 1986, Science 232:518–521; Radeke et al., 1987, Nature 325:593–597). In addition to the LNGFR another protein (designated "HNGFR" for high-affinity NGF receptor), which is involved in forming a higher affinity binding site for NGF, is apparently required to initiate NGF-induced signal transduction (Zimmerman et al., 1978, J. Supramol. Struc. 92:351–361; Sutter et al., 1979 in Transmembrane Signalling (N.Y. Alan Liss) pp. 659–667; Bernd and Greene, 1984, J. Bio. Chem. 259:15509–15516; Hempstead et al., 1989, Science 243:373–375). This HNGFR is phosphorylated on tyrosine in response to NGF, and apparently contains intrinsic tyrosine kinase activity (Meakin and Shooter, 1991a, Neuron 6:153–163). Furthermore, early intermediates in tyrosine kinase activated signal cascades, the ERK kinases (also known as the MAP2 kinases), are rapidly activated and phosphorylated on tyrosine in response to NGF. Thus, like many other growth factor responses, NGF signal transduction may be initiated by the activation of a receptor-linked tyrosine kinase.

Recent studies have revealed that the product of the trk proto-oncogene, which resembles a growth factor receptor (i.e., it is a transmembrane protein containing an intracytoplasmic tyrosine kinase domain) for which no ligand had been identified, is rapidly phosphorylated in response to NGF treatment in PC12 cells (Kaplan et al., 1991, Nature 350:156–160; Klein et al., 1991, Cell 65:189–197) and to directly bind NGF with relatively high affinity when expressed in heterologous cells (Klein et al. supra. This finding, together with the restricted neuronal distribution of the trk protein in vivo, suggests that trk may be the component of the HNGFR responsible for initiating NGF signal transduction.

In contrast to the extensive study of NGF receptors and signal transduction pathways, the receptors and signal transduction pathways utilized by the other neurotrophic factors have only recently begun to be explored. However, BDNF appears to bind to the LNGFR with an affinity similar to that of NGF (Rodriguez-Tebar et al., 1990, Neuron 4:487–492). Although both low and high affinity receptors for BDNF exist on neurons responsive to BDNF, the findings that BDNF and NGF act on different neurons and that NGF-responsive neurons do not express high-affinity BDNF receptors suggest that BDNF utilizes a different high affinity receptor than NGF (Rodriguez-Tebar and Barde, 1988, J. Neurosc. 8:3337–3342).

A variety of findings seem to link BDNF and NT-3, while distinguishing both of these neurotrophins from NGF. NT-3 and BDNF (but not NGF) expression displays striking reciprocal relationships during development, with NT-3 being expressed more prominently early and BDNF more prominently late during the development of some of the same brain regions (Maisonpierre et al., 1990, Neuron 5: 501–509). Interestingly, the distribution profiles that BDNF and NT-3 (but not NGF) ultimately achieve in various adult brain regions are quite similar. Id. In peripheral ganglia both BDNF and NT-3 (but not NGF) have their most prominent effects on dorsal root ganglia and nodose ganglia, although NT-3 does seem to have minor effects on sympathetic ganglia (Maisonpierre et al. 1990a, Science 247: 1446–1451)

These findings led to the suggestion that BDNF and NT-3 might in some cases act on the same neuronal populations, and that an early effect of NT-3 on these neurons might be replaced by a later effect of BDNF (Maisonpierre et al., 1990b, Neurons 52:501–509). Furthermore, the finding that BDNF and NT-3 (but not NGF) are the most highly conserved growth factors yet described led to the suggestion that both these factors might be interacting with multiple receptors and that their strict conservation was required to maintain the specificity of their interactions with these multiple receptors.

Klein et al. (1989, EMBO J. 8:3701–3709) reported the isolation of trkB, which encoded a new member of the tyrosine protein kinase family of receptors found to be highly related to the human trk protooncogene (FIG. 8A–D). At the amino acid level, the products of trk and trkB were found to share 57 percent homology in their extracellular regions, including 9 of the 11 cysteines present in trk. This homology was found to increase to 88 percent within their respective tyrosine kinase catalytic domains. In adult mice, trkB was found to be preferentially expressed in brain tissue, although significant levels of trkB RNAs were also observed in lung, muscle, and ovaries. Further, trkB transcripts were detected in mid and late gestation embryos. In situ hybridization analysis of 14 and 18 day old mouse embryos indicated that trkB transcripts were localized in the central and peripheral nervous systems, including brain, spinal cord, spinal and cranial ganglia, paravertebral trunk of the sympathetic nervous system and various innervation pathways, suggesting that the trkB gene product may be a receptor involved in neurogenesis and early neurol development as well as playing a role in the adult nervous system.

In 1990, Klein et al. (Cell 61:647–656) reported that the mouse trkB locus codes for at least two classes of receptor-like molecules, which they designated gp145$^{trkB}$ and gp95$^{trkB}$. These molecules appeared to have identical extracellular and transmembrane domains, but only gp145$^{trkB}$ was found to contain a long cytoplasmic region that included a catalytic protein kinase domain. TrkB transcripts coding for this protein were observed in the cerebral cortex and the pyramidal cell layer of the hippocampus, whereas transcripts encoding gp95$^{trkB}$ were found in the ependymal linings of the cerebral ventricles and in the choroid plexus. Further, Middlemas et al. (1991, Mol. Cell. Biol. 11:143–153) reported the existence of two distinct C-terminally truncated receptors which share the complete extracellular region and transmembrane domain with gp145$^{trkB}$ but which differ from gp145$^{trkB}$ (hitherto referred to simply as trkB) in their short cytoplasmic tails.

3. SUMMARY OF THE INVENTION

The present invention provides for assay systems that may be used to detect and/or measure neurotrophin activity or to identify agents that exhibit neurotrophin-like activity, and for methods of using such assay systems. It is based, at least in part, on the discovery that the trkB proto-oncogene encodes a tyrosine kinase receptor that may serve as a functional binding protein for BDNF and NT-3. Such assay systems may be of particular value in identifying new neurotrophins or agents with neurotrophin-like activity. In various embodiments, the assay systems and methods of the invention may be used to detect and/or measure the binding of neurotrophin to the trkB protein, either using direct binding studies or the detection of the secondary effects of trkB/neurotrophin binding.

The present invention also provides for systems that may be used in both the assay of pre-defined agents, as well as the discovery of novel agents, that act on receptor tyrosine kinases. In a related aspect of this invention, the same system can be used to discover unknown receptors that mediate responses to known factors. This invention is based, at least in part, on the discovery that the trkB proto-oncogene encodes a tyrosine kinase receptor that is able not only to mediate BDNF/NT-3 dependent neuronal survival and differentiation (and not proliferation) in the neuronal cells in which it is normally expressed, but also is able to confer BDNF/NT-3 dependent survival and proliferation when stably expressed in a particular clone of the NIH3T3 fibroblast cell line. Thus, according to the invention, the expression of receptor tyrosine kinases in fibroblasts allows for the use of these cells in survival/proliferation assays that may be used in both the assay of pre-defined agents, (such as the neurotrophins) as well as the discovery of novel agents, that act on these receptor tyrosine kinases; or other receptor tyrosine kinases for which no known ligand exists; these systems can be used even with receptor/ligand systems (such as the trk receptors and the neurotrophins) which may not normally act to mediate cellular proliferation. Once a particular receptor/ligand system is defined (as is done here with trkB and BDNF/NT-3), a variety of additional specific assay systems can be utilized.

The present invention also has diagnostic and therapeutic utilities. In particular embodiments of the invention, methods of detecting aberrancies in trkB function or expression may be used in the diagnosis of neurological disorders. In other embodiments, manipulation of the trkB/neurotrophin interaction may be used in the treatment of neurological disorders, including Alzheimer's disease, Parkinson's disease, and amyotrophic lateral sclerosis (Lou Gehrig's disease).

| 3.1. ABBREVIATIONS | |
|---|---|
| BDNF | brain derived neurotrophic factor |
| BSA | bovine serum albumin |
| CNTF | ciliary neurotrophic factor |
| DSS | Disuccinimidyl suberate |
| HNGFR | high affinity nerve growth factor receptor |
| LNGFR | low affinity nerve growth factor receptor |
| NGF | nerve growth factor |
| NT-3 | neurotrophin 3 |
| pCMX-LNGFR | pCMX expression vector for expression |
| pCMX-trkB | pCMX expression vector modified for expression of full length rat trkB cDNA |
| pCMX-trkB(del) | modified form of pCMX-trkB designed to express truncated form of trkB lacking most of the intracytoplasmic tyrosine kinase domain |
| pT24-ras | plasmid contained mutated (activated) version of ras oncogen |

4. DESCRIPTION OF THE FIGURES

Figure 1B:
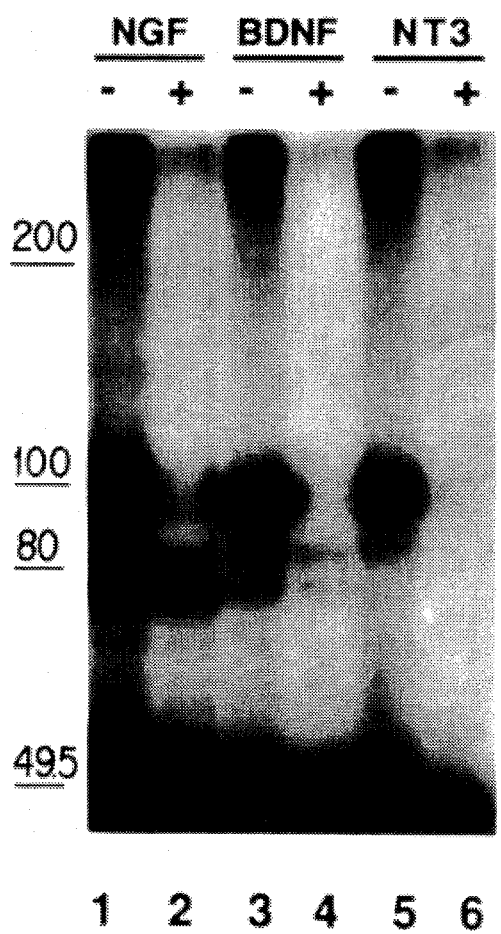
Figure 1C:
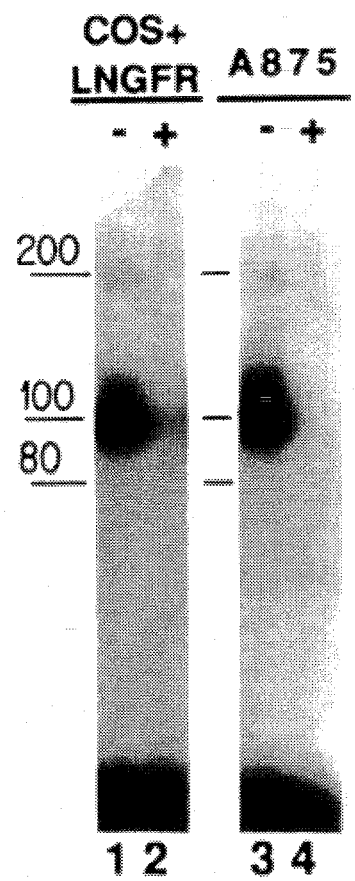

FIGS. 1A–C. All three neurotrophins specifically cross-link to the LNGFR expressed in COS cells.

A. None of the neurotrophins display competable cross-linking to COS cells transfected with control vector, pCMX. The radiolabeled ligand utilized for each pair of lanes is indicated at top of lanes (each radiolabeled ligand is estimated to be at a concentration between 0.1 and 0.25 nM); "–" indicates absence and "+" indicates presence of unlabeled homologous ligand at a concentration of 500 nM. Notable bands seen with radiolabeled NGF varied from experiment to experiment and were not competable with unlabeled NGF, as indicated.

B. All three radiolabeled neurotrophins display competable cross-linking (resulting in a complex of approximately 100 kD, as expected for LNGFR) in COS cells transfected with pCMX-LNGFR; lanes marked as in panel A.

C. Cross-linked species in COS cells transfected with pCMX-LNGFR co-migrates with cross-linked species in human A875 melanoma cells. Radiolabeled ligand used in this panel was BDNF; cells used for cross-linking indicated at top of each pair of lanes, and "–" and "+" as in panel A.

Figure 2A:
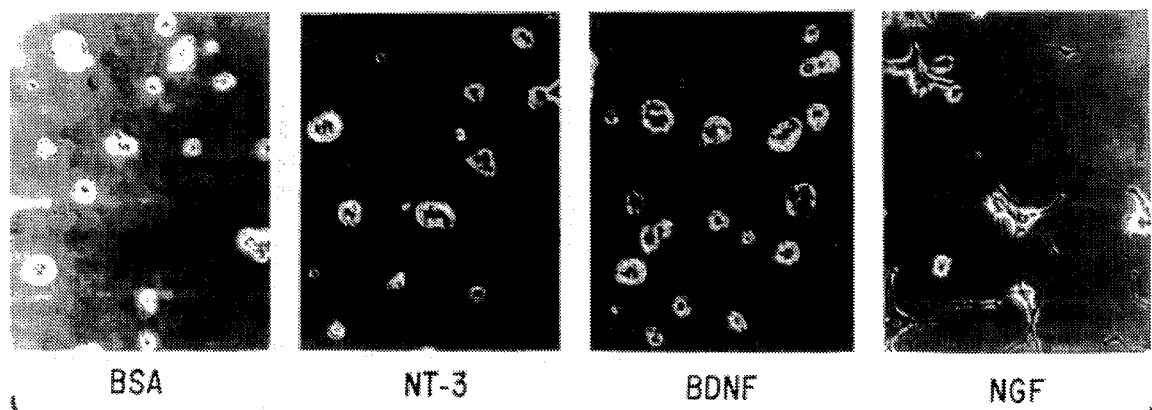
Figure 2B:
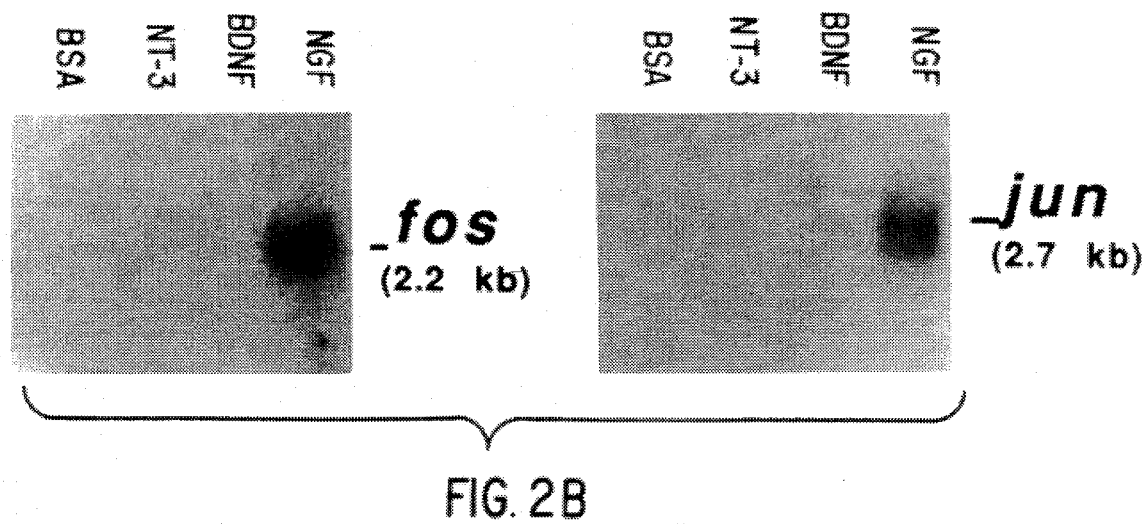

FIGS. 2A–B. Induction of neurite outgrowth and immediate-early gene expression in PC12 cells in response to NGF but not BDNF or NT-3.

A. PC12 cells cultured as recommended by Greene et al., 1987, Methods Enzymol. 147:, 207–216 in the presence of 100 ng/ml of BSA, NT-3, BDNF or NGF, as indicated. Varying concentrations of neurotrophins were tried; concentrations deemed saturating for NGF are depicted.

B. fos and jun transcripts (2.2 and 2.7 kb, respectively) identified by Northern analysis of total cellular RNA prepared from PC12 cells cultured as above in the absence of exogenous neurotrophic factors, and then treated for 30 minutes with 100 ng/ml BSA, NT-3, BDNF or NGF as indicated.

FIGS. 3A–B. BDNF and NT-3, but not NGF, bind specifically to trkB expressed in COS cells.

A. COS cells transfected with pCMX-trkB and chemically cross-linked to each of the three radiolabeled neurotrophins. Radiolabeled ligand utilized for each pair of lanes is indicated at top of lanes (each radiolabeled ligand is estimated to be at a concentration between 0.1 and 0.25 nM); "–" indicates absence and "+" indicates presence of unlabeled homologous ligand at a concentration of 500 nM. Bracket and asterisk indicate cross-linked species corresponding to trkB protein (approximately 160 to 180 kD).

B. Cross-linking of radiolabeled NT-3, in the absence ("–") or presence ("+") of unlabeled NT-3 at 500 nM, to COS cells transfected with an expression vector for a truncated form (lacking the tyrosine kinase domain) of trkB (pCMX-trkB(del)). Bracket and asterisk indicate cross-linked species corresponding to truncated version of trkB (120 to 150 kD, as expected for this deletion mutant).

FIGS. 4A–D. Cross-linking and binding of $^{125}$I-NT-3 to LNGFR is specifically blocked by all three neurotrophins, while cross-linking and binding of NT-3 to trkB is specifically blocked only by BDNF and NT-3.

A. COS cells transfected with pCMX-LNGFR and cross-linked to radiolabeled NT-3 (estimated concentration between 0.1 to 0.25 nM); the unlabeled neurotrophin used as cold competitor is indicated at the top of each triplet of lanes, with the concentration used per lane (in nM) indicated.

B. COS cells transfected with pCMX-trkB and cross-linked to radiolabeled NT-3; ligand concentrations and lane markings as in panel A.

C. COS cells transfected with pCMX-LNGFR used in solution binding experiments with radiolabeled NT-3 (at a concentration estimated to be between 0.1 and 0.25 nM) competed with varying concentrations of unlabeled NT-3, BDNF and NGF, as indicated.

D. COS cells transfected with pCMX-trkB used in solution binding experiments with radiolabeled NT-3 (at a concentration estimated to be between 0.1 and 0.25 nM) competed with varying concentrations of unlabeled NT-3, BDNF and NGF, as indicated. Date represent the percentage of total cpm bound and are the average of duplicate assays.

FIGS. 5A–E. PC12 cells transfected with pCMX-trkB differentiate in the presence of BDNF and NT-3.

A. PC12 cells transiently transfected with control plasmid pT24-ras and treated with 100 ng/ml BSA, used to determine number of transiently transfected cells in each experiment (see text for details).

B, C, D and E. PC12 cells transiently transfected with pCMX-trkB and treated with 100 ng/ml NGF (panel B), BSA (panel C), NT-3 (panel D) or BDNF (panel E). Numbers (in parentheses) at the bottom of each panel indicate the number of differentiated PC12 cells (i.e. cells having neurites more than twice the length of the cell body) observed per 35 mm well following each treatment; although absolute numbers varied in the three transfections performed, the ratios of differentiated cells observed following the different treatments remained constant for three independent experiments. No differentiated cells were observed in pCMX-trkB transfected PC12 cells treated with BSA (three separate experiments); after electroporation the cells were plated directly on plastic without pre-coating to eliminate any background neurite outgrowth, as described in text and in the Experimental Procedures.

Figure 6A:
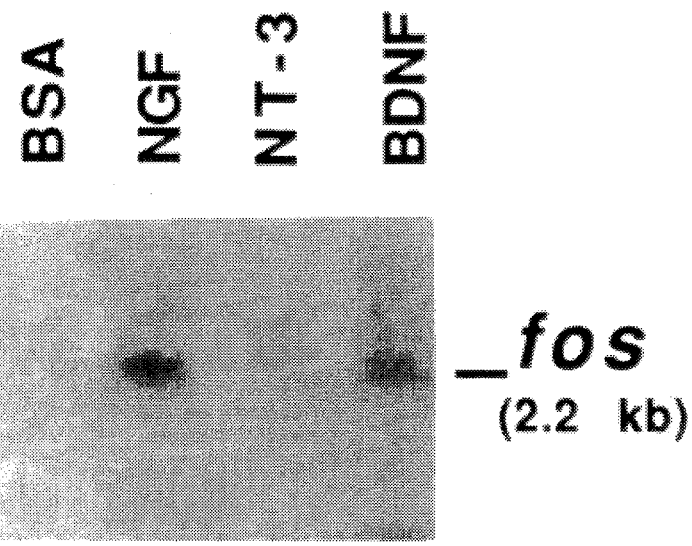
Figure 6B:
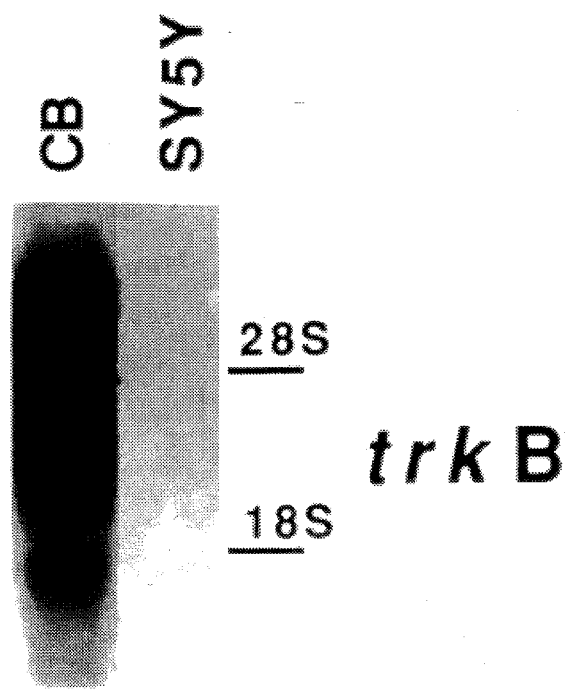

FIGS. 6A–B. The human neuroblastoma SH-SY5Y responds to NGF and BDNF but not NT-3, and does not express trkB.

A. fos transcripts identified by Northern analysis of total cellular RNA prepared from SH-SY5Y cells cultured in the absence of added factor, and then treated for 30 minutes with 100 ng/ml BSA, NGF, NT-3, or BDNF as indicated.

B. trkB transcripts are detected by Northern analysis using ten micrograms of total cellular RNA from adult rat cerebellum (designated CB), but are not detectable in ten micrograms of total cellular RNA from SH-SY5Y. The complete coding region of trkB was used as a probe which identifies multiple trkB transcripts (Klein et al., 1989, EMBO J. 8: 3701–3709); the cerebellum lane appears as a smear because of gross over-exposure in the attempt to detect transcripts in SH-SY5Y.

Figure 7:
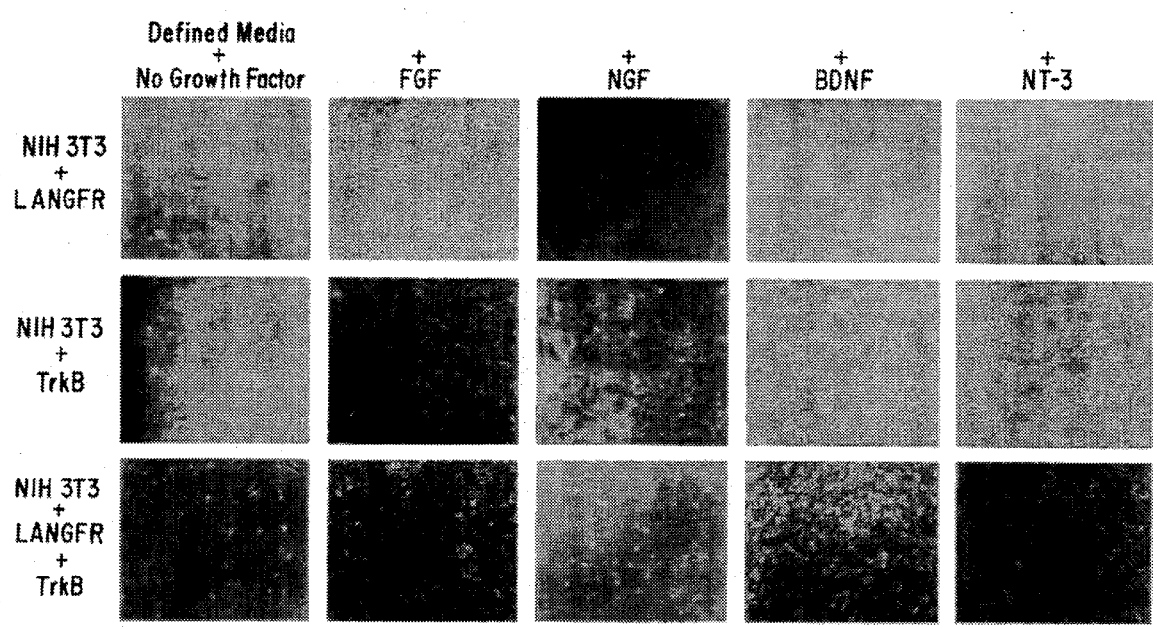

FIG. 7. Growth factor dependent 3T3 cells expressing introduced genes encoding either LANGFR (row 1), trkB (row 2) or LANGFR and trkB (row 3).

FIGS. 8A–D. cDNA and amino acid sequence of mouse trkB (SEQ ID NO:1, and SEQ. ID No: 2) as described in Klein, et al. (1989, EMBO J. 8:3701–3709).

FIGS. 8A–D. cDNA and amino acid sequence of mouse trkB (SEQ ID NO:1, and SEQ. ID No: 2) as described in Klein, et al. (1989, EMBO J. 8:3701–3709).

5. DETAILED DESCRIPTION OF THE INVENTION

For purposes of clarity of disclosure, and not by way of limitation, the detailed description of the invention is divided into the following subsections:

(i) assay systems and methods;

(ii) experimental model systems;

(iii) diagnostic methods;

(iv) therapeutic methods; and (v) systems for the assay and discovery of agents that act on receptor tyrosine kinases.

5.1. ASSAY METHODS AND SYSTEMS
5.1.1. METHODS

The present invention provides for assay systems and methods that may be used to detect and/or measure neurotrophin activity or to identify agents that exhibit neurotrophin-like activity. The term "neurotrophin activity," as used herein, should be construed to refer to the activity of BDNF or NT-3, or of other, hitherto unidentified neurotrophic factors, or of non-neurotrophic factors (including peptide and nonpeptide molecules) which are capable of binding to trkB. Agents that exhibit neurotrophin activity include but are not limited to neurotrophic and non-neurotrophic factors, including peptide and non-peptide molecules, that have biological activity similar to BDNF and/or NT-3 with respect to immediate early gene induction, cell types affected, phenomena induced, etc. Biological activities of BDNF and NT-3 are described, respectively, in PCT application numbers PCT/US90/04915 and PCT/US90/04916, which are incorporated by reference in their entirety herein. Henceforth, both neurotrophins and agents with neurotrophin activity will be collectively referred to as test agents.

Accordingly, the present invention provides for a method of detecting or measuring neurotrophin activity comprising (i) exposing a cell that expresses trkB to a test agent; and (ii) detecting or measuring the specific binding of the test agent to trkB, in which specific binding to trkB positively correlates with neurotrophin activity.

A cell that expresses trkB may either naturally express trkB or be genetically engineered to do so. For example, trkB-encoding nucleic acid sequences obtained as described in section 6.1.2., infra, may be introduced into a cell by transfection, transduction, microinjection, electroporation, via a transgenic animal, etc., using any method known in the art. See for example, the transfection of COS and PC12 cells as described in section 6, infra, and the description of assay systems provided in Section 5.1.2., infra.

The specific binding of test agent to trkB may be measured in a number of ways. For example, the actual binding of test agent to cells expressing trkB may be detected or measured, by detecting or measuring (i) test agent bound to the surface of intact cells; (ii) test agent cross-linked to trkB protein in cell lysates; or (iii) test agent bound to trkB in vito. The specific interaction between test agent and trkB may be evaluated by using reagents that demonstrate the unique properties of that interaction. For example, it has been demonstrated, according to the present invention (see section 6) that BDNF and NT-3, but not NGF, bind to trkB. Therefore, the specific binding of test agent to trkB may be competitively inhibited by BDNF or NT-3, but not NGF.

As a specific, nonlimiting example, the methods of the invention may be used as follows. Consider a case in which the neurotrophin level (for instance, BDNF) in a sample is to be measured. Varying dilutions of the sample (the test agent), in parallel with a negative control (NC) containing no BDNF activity, and a positive control (PC) containing a known amount of BDNF, may be exposed to cells that express trkB in the presence of detectably labeled BDNF (in this example, radioiodinated BDNF). The amount of BDNF in the test sample may be evaluated by determining the amount of $^{125}$I-labeled BDNF that binds to the controls and in each of the dilutions, and comparing the sample values to a standard curve. The more BDNF in the sample, the less $^{125}$I-BDNF that will bind to trkB. The amount of $^{125}$I-BDNF bound may be determined by measuring the amount of radioactivity per cell, or by cross-linking the BDNF to cell surface proteins using DSS, as described in Meakin and Shooter, 1991, Neuron 6:153–163, and detecting the amount of labeled protein in cell extracts, using, for example, SDS polyacrylamide gel electrophoresis, which may reveal a labeled protein having a size corresponding to BDNF-bound trkB. The specific test agent/trkB interaction may further be tested by adding various dilutions of unlabeled NGF to the assays; such unlabeled NGF should have no substantial affect on the competition between labeled BDNF and test agent for trkB binding. Alternatively, an agent known to be able to disrupt neurotrophin/trkB binding, such as, but not limited to, unlabeled NT-3 or anti-trkB antibody, may be expected to interfere with the competition between $^{125}$I-BDNF and test agent for trkB binding.

Detectably labeled neurotrophin includes, but is not limited to, neurotrophin linked covalently or noncovalently to a radioactive substance, a fluorescent substance, a substance that has enzymatic activity, a substance that may serve as a substrate for an enzyme (enzymes and substrates associated with colorimetrically detectable reactions are preferred) or to a substance that can be recognized by an antibody molecule that is preferably a detectably labeled antibody molecule.

Alternatively, the specific binding of test agent to trkB may be measured by evaluating the secondary biological effects of neurotrophin/trkB binding, including, but not limited to, the induction of neurite sprouting, immediate early gene expression or phosphorylation of trkB (see FIG. 8). For example, the ability of the test agent to induce neurite sprouting can be tested in cells that lack trkB and in comparable cells that express trkB; neurite sprouting in trkB expressing cells but not in comparable cells that lack trkB would be indicative of a specific test agent/trkB interaction. A similar analysis could be performed by detecting immediate early gene (e.g. fos and jun) induction in trkB-minus and trkB-plus cells, or by detecting phosphorylation of trkB using standard phosphorylation assays known in the art. Such analysis might be useful in identifying neurotrophin agonists or antagonists that do not competitively bind to trkB.

For example, and not by way of limitation, it may be desirable to determine whether a particular sample contains BDNF. PC12 cells, a well characterized neuroblastoma cell line, do not sprout neurites in response to BDNF treatment (see section 6, infra, and FIG. 2A). However, PC12 cells transfected with trkB do sprout neurites in response to BDNF (see section 6, infra, and FIG. 5). Therefore, normal PC12 cells (trkB-minus cells) and PC12 cells transfected with trkB (trkB-plus cells) may be exposed to the sample (the test agent) and the presence or absence of neurite sprouting may be evaluated microscopically. In other embodiments, the amount of BDNF in the sample may be measured by determining the amount of neurite sprouting (or immediate early gene induction) and then comparing this value with a dose response curve for the particular neurotrophin being tested, here, BDNF.

Similarly, the present invention provides for a method of identifying an agent that has neurotrophin activity comprising (i) exposing a cell that expresses trkB to a test agent and (ii) detecting the specific binding of the test agent to trkB, in which specific binding to trkB positively correlates with neurotrophin-like activity. Specific binding may be detected by either assaying for direct binding or the secondary biological effects of binding, as discussed supra. such a method may be particularly useful in identifying new members of the neurotrophin family or, in the pharmaceutical industry, in screening a large array of peptide and non-peptide agents (e.g., peptidomimetics) for neurotrophin-like activity. In a preferred, specific, nonlimiting embodiment of the invention, a large grid of culture wells may be prepared that contain, in alternate rows, PC12 cells that are either trkB-minus or engineered to be trkB-plus. A variety of test agents may then be added such that each column of the grid, or a portion thereof, contains a different test agent. Each well could then be scored for the presence or absence of neurite sprouting. An extremely large number of test agents could be screened for neurotrophin activity in this manner.

In additional embodiments, the invention provides for methods of detecting or measuring neurotrophin activity or identifying an agent as having neurotrophin activity comprising (i) exposing a test agent to a trkB protein in vitro under conditions that permit binding to occur and (ii) detecting binding of the test agent to the trkB protein, in which binding of test agent to trkB correlates with neurotrophin or neurotrophin-like activity. According to such methods, the trkB may or may not be substantially purified, may be affixed to a solid support (e.g. as an affinity column or as an ELISA assay), or may be incorporated into an artificial membrane. Binding of test agent to trkB may be evaluated by any method known in the art. In preferred embodiments, the binding of test agent may be detected or measured by evaluating its ability to compete with detectably labeled known trkB ligands for trkB binding.

The present invention also provides for a method of detecting the ability of a test agent compound to function as an antagonist of neurotrophin activity comprising detecting the ability of the compound to inhibit an effect of neurotrophin binding to trkB on a cell that expresses trkB. Such an antagonist may or may not interfere with trkB/neurotrophin binding. Effects of neurotrophin binding to trkB are preferably biological or biochemical effects, including, but not limited to, neurite sprouting, cell survival or proliferation, cell transformation, immediate early gene induction, or trkB phosphorylation. For example, and not by way of limitation, PC12 cells transfected with trkB may be exposed to effective amounts of either BDNF or BDNF plus a test agent suspected of being a BDNF antagonist. Neurite sprouting in these two groups of cells may be compared to sprouting in non-transfected PC12 cells exposed to BDNF, or BDNF plus the test agent, or NGF, or NGF plus the test agent. If the antagonist specifically inhibits BDNF, neurite sprouting should be inhibited only in trkB plus PC12 cells treated with BDNF plus test agent compared to trkB plus PC12 cells exposed to BDNF, and there should be little or no inhibition of sprouting of trkB-minus PC12 cells treated with NGF plus test agent relative to trkB-minus PC12 cells treated with NGF alone.

5.1.2. SYSTEMS

The present invention also provides for assay systems that may be used according to the methods described supra. Such assay systems may comprise in vitro preparations of trkB, e.g. affixed to a solid support, or may, preferably, comprise cells that express trkB protein.

Cells that express trkB protein may do so naturally or may be genetically engineered to produce trkB, as described supra, by transfection, transduction, electroporation, microinjection, via a transgenic animal, etc. of nucleic acid encoding trkB in a suitable expression vector.

Any of the methods known to one skilled in the art for the insertion of DNA fragments into a vector may be used to construct expression vectors encoding trkB containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding trkB protein or peptide fragment may be regulated by a second nucleic acid sequence so that trkB protein or peptide is expressed in a host transformed with the recombinant DNA molecule. For example, expression of trkB may be controlled by any promoter/enhancer element known in the art. Promoters which may be used to control trkB expression include, but are not limited to, the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothioein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADH (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkeft et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing trkB gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted trkB gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the trkB gene is inserted within the marker gene sequence of the vector, recombinants containing the trkB insert can be identified by the absence of the marker gene function. In the third approach, recombinant expression vectors can be identified by assaying the foreign gene product expressed by the recombinant. Such assays can be based, for example, on the physical or functional properties of the trkB gene product, for example, by binding of the receptor to neurotrophic factor or to an antibody which directly recognizes the trkB. Cells of the present invention may transiently or, preferably, constitutively and permanently express trkB.

In preferred embodiments, the present invention provides for cells that express trkB and that also contain recombinant nucleic acid comprising an immediate early gene promoter (e.g. the fos or jun promoters (Gilman et al., 1986, Mol. Cell. Biol. 6:4305–4316). When such a cell is exposed to a neurotrophin, the neurotrophin may be expected to bind to trkB and secondarily induce transcription off the immediate early promoter. Such a cell may be used to detect neurotrophin/trkB binding by measuring the transcriptional activity of the immediate early gene promoter, for example, by nuclear run-off analysis, Northern blot analysis, or by measuring levels of a gene controlled by the promoter. The immediate early promoter may be used to control the expression of fos or jun or any detectable gene product, including, but not limited to, any of the known reporter genes, such as chloramphenicol acetyltransferase (CAT), neomycin phosphotransferase (neo), beta-galactosidase beta-glucuronidase, beta-galactosidase, etc. In a specific embodiment, neurotrophin/trkB binding in a cell that expresses trkB and contains the human growth hormone gene under the control of the fos gene promoter may be expected to produce recombinant human growth hormone, as measured by Seldon et al., 1986, Mol. Cell. Biol. 6:3173–3179. In another embodiment, trkB expression may also be used as a reporter gene and be placed under the control of an immediate early promoter in addition to constitutively expressed trkB to produce an amplified response to neurotrophin. Such trkB-expression reporter gene containing cell lines may provide an exceptionally sensitive and efficient method of detecting or measuring neurotrophin activity.

Furthermore, the cells used in the assay systems of the invention may or may not be cells of the nervous system. For example, in a specific, nonlimiting embodiment of the invention, growth-factor dependent fibroblasts may be used as the basis for a neurotrophin assay system. See Section 7, infra, and FIG. 7. A fibroblast cell line that is growth factor dependent in serum-free media (e.g. as described in Zham and Goldfarb, 1986, Mol. Cell. Biol. 6:3541–3544) may be transfected with the trkB gene, for instance by using a $CaPO_4$ transfection protocol with 5 micrograms of DNA of CMV-promoter-based expression vector comprising the rat trkB gene and one microgram of hygromycin-resistance gene-containing expression vector. After about 48 hours, the cells may then be selected for hygromycin resistance to identify positive transfectants. The cells may then be cultured for about three weeks in the presence of hygromycin, and then resistant colonies may be pooled. These cells may then be plated on tissue culture plates coated with poly-D-lysine and human fibronectin, and allowed to grow in DMEM plus 10% bovine calf serum for about four hours to allow the cells to bind to the plates. The serum-containing media may then be aspirated and the cells may be washed about three times with PBS to remove any residual serum. The cells may then be taken up with either serum free defined media (A 3:1 mixture of DMEM and Hams F12, supplemented with 8 mM sodium bicarbonate, 15 mM HEPES, $4\times10^{-6}$M $MnCl_2$, 3 mM histidine, $10^{-5}$M ethanolamine, $10^{-7}$M sodium selenite, 5 mg transferrin per liter, 200 mg bovine serum albumin-linoleic acid complex per liter gentamicin, penicillin, and streptomycin, 20 mM L-glutamine). Cells produced in this manner, then incubated with neurotrophin (e.g. 100 ng/ml NT-3 or BDNF), may, after about 5 days in culture (replacing media and growth factors every 48 hours), be expected to be growing and proliferating; cells treated with NGF at 100 ng/ml or in serum free-medium should not, however, proliferate (see also FIG. 7). As discussed in Section 6, infra, data suggests that there is another, non-trkB receptor for BDNF expressed on SH-SY5Y cells (see also FIG. 6). The present invention also provides for assay systems and methods utilizing the non-trkB receptor in a manner analogous to those utilizing the trkB receptor, as described herein.

5.2. EXPERIMENTAL MODEL SYSTEMS

The present invention also provides for experimental model systems for studying the physiological role of the neurotrophin gene family. In these model systems, trkB protein, peptide fragment, or a derivative thereof, may be either supplied to the system or produced within the system. Such model systems could be used to study the effects of neurotrophin excess or neurotrophin depletion. The experimental model systems may be used to study the effects of increased or decreased response to neurotrophin in cell or tissue cultures, in whole animals, in particular cells or tissues within whole animals or tissue culture systems, or over specified time intervals (including during embryogenesis) in embodiments in which trkB expression is controlled by an inducible or developmentally regulated promoter. In particular embodiments of the invention, the CMV promoter may be used to control expression of trkB in transgenic animals. The term "transgenic animals," as used herein, refers to non-human transgenic animals, including transgenic mosaics, which carry a transgene in some or all of their cells, which include any non-human species, and which are produced by any method known in the art, including, but not limited to microinjection, cell fusion, transfection, electroporation, etc. For example, the animals may be produced by a microinjection of zygotes by a method such as that set forth in "Brinster et al., 1989, Proc. Natl. Acad. Sci. U.S.A. 82:4438–4442.

The present invention also provides for model systems for autoimmune disease in which an autoimmune response is directed toward trkB. Such models comprise animals which have been immunized with immunogenic amounts of trkB and preferably found to produce anti-trkB antibodies and/or cell-mediated immunity. To produce such a model system, it may be desirable to administer the trkB in conjunction with an immune adjuvant, such as Bacille Calmette Guerin (BCG).

5.2.1. MODELS FOR INCREASED NEUROTROPHIN ACTIVITY

For example, and not by way of limitation, an experimental model system may be created which may be used to study the effects of excess neurotrophin activity. In such a system, the response to neurotrophin may be increased by engineering an increased number of trkB molecules on cells of the model system relative to cells which have not been so engineered. It may be preferable to provide an increased number of neurotrophins selectively on cells which normally express neurotrophins.

Cells may be engineered to produce increased amounts of trkB protein by infection with a virus which carries a trkB gene of the invention. Alternatively, the trkB gene may be provided to the cells by transfection.

If the model system is an animal, a recombinant trkB gene may be introduced into the cells of the animal by infection with a virus which carries the trkB gene. Alternatively, a transgenic animal may be created which carries the trkB gene as a transgene.

In order to ensure expression of trkB, the trkB gene should be placed under the control of a suitable promoter sequence. It may be desirable to put the trkB gene under the control of a constitutive and/or tissue specific promoter, including but not limited to the CNS neuron specific enolase, neurofilament, and tyrosine hydroxylase D promoter, an inducible promoter, such as the metallothionein promoter, the UV activated promoter in the human immunodeficiency virus long terminal repeat (Valeri et al., 1988, Nature 333:78–81), or the CMV promoter (as contained in pCMX, infra) or a developmentally regulated promoter.

By increasing the number of cellular trkB molecules, the response to endogenous neurotrophin may be increased. If the model system contains little or no neurotrophin, neurotrophin may be added to the system. It may also be desirable to add additional neurotrophin to the model system in order to evaluate the effects of excess neurotrophin activity. Over expressing neurotrophin (or secreted neurotrophin) may be the preferable method for studying the effects of elevated levels of neurotrophin on cells already expressing trkB. More preferably would be to express trkB in all cells (general expression) and determine which cells are then endowed with functional responsiveness to neurotrophin, thus allowing the potential identification of a second receptor component, if one exists.

5.2.2. MODELS FOR DECREASED NEUROTROPHIN ACTIVITY

Alternatively, as an example, and not by way of limitation, an experimental model system may be created which may be used to study the effects of diminished neurotrophin activity. This system may permit identification of processes or neurons which require neurotrophin, and which may represent potential therapeutic targets. In such a system, the response to neurotrophin may be decreased by providing recombinant trkB proteins which are not associated with a cell surface or which are engineered so as to be ineffective in transducing a response to neurotrophin.

For example, trkB protein, peptide, or derivative may be supplied to the system such that the supplied receptor may compete with endogenous trkB for neurotrophin binding, thereby diminishing the response to neurotrophin. The trkB may be a cell free receptor which is either added to the system or produced by the system. For example, a trkB protein which lacks the transmembrane domain may be produced by cells within the system, such as an anchorless trkB that may be secreted from the producing cell. Alternatively, trkB protein, peptide or derivative may be added to an extracellular space within the system.

In additional embodiments of the invention, a recombinant trkB gene may be used to inactivate or "knock out" the endogenous gene by homologous recombination, and thereby create a trkB deficient cell, tissue, or animal. For example, and not by way of limitation, a recombinant trkB gene may be engineered to contain an insertional mutation, for example the neo gene, which inactivates trkB. Such a construct, under the control of a suitable promoter, may be introduced into a cell, such as an embryonic stem cell, by a technique such as transfection, transduction, injection, etc. Cells containing the construct may then be selected by G418 resistance. Cells which lack an intact trkB gene may then be identified, e.g. by Southern blotting or Northern blotting or assay of expression. Cells lacking an intact trkB gene may then be fused to early embryo cells to generate transgenic animals deficient in trkB. A comparison of such an animal with an animal not expressing endogenous neurotrophin would reveal that either the two phenotypes match completely or that they do not, implying the presence of additional neurotrophin-like factors or receptors.

Such an animal may be used to define specific neuronal populations, or any other in vivo processes, normally dependent upon neurotrophin. Thus, these populations or processes may be expected to be affected if the animal did not express trkB and therefore could not respond to neurotrophin.

Alternatively, a recombinant trkB protein, peptide, or derivative which competes with endogenous receptor for neurotrophin may be expressed on the surface of cells within the system, but may be engineered so as to fail to transduce a response to neurotrophin binding.

The recombinant trkB proteins, peptides or derivatives described above may bind to neurotrophin with an affinity that is similar to or different from the affinity of endogenous trkB to neurotrophin. To more effectively diminish the response to neurotrophin, the trkB protein, peptide, or derivative may desirably bind to neurotrophin with a greater affinity than that exhibited by the native receptor.

If the trkB protein, peptide, or derivative is produced within the model system, nucleic acid encoding the trkB protein, peptide, or derivative may be supplied to the system by infection, transduction, transfection, etc. or as a transgene. As discussed supra, the trkB gene may be placed under the control of a suitable promoter, which may be, for example, a tissue-specific promoter or an inducible promoter or developmentally regulated promoter.

In a specific embodiment of the invention, the endogenous trkB gene of a cell may be replaced by a mutant trkB gene by homologous recombination. In another embodiment of the invention, a test animal may be immunized against trkB.

In a further embodiment of the invention, trkB expression may be reduced by providing trkB expressing cells with an amount of trkB anti-sense RNA or DNA effective to reduce expression of trkB protein.

5.3. DIAGNOSTIC APPLICATIONS

According to the present invention, trkB probes may be used to identify cells and tissues which are responsive to neurotrophin in normal or diseased states. The present invention provides for a method of diagnosing a neurological disorder in a patient comprising comparing the levels of expression of trkB in a patient sample with the levels of expression of trkB in a comparable sample from a healthy person, in which a difference in the levels of expression of trkB in the patient compared to the healthy person indicates that a disorder in the patient may be primarily or secondarily related to trkB metabolism. A patient sample may be any cell, tissue, or body fluid but is preferably nervous system tissue or cerebral spinal fluid. The present invention provides for methods for identifying cells which are responsive to neurotrophin comprising detecting trkB expression in such cells. TrkB expression may be evidenced by transcription of trkB mRNA or production of trkB protein. TrkB expression may be detected using probes which identify trkB nucleic acid or protein.

Yet another variety of probe which may be used is anti-trkB antibody or fragments thereof containing the binding domain.

According to the invention, trkB protein, or fragments or derivatives thereof, may be used as an immunogen to generate anti-trkB antibodies. By providing for the production of relatively abundant amounts of trkB protein using recombinant techniques for protein synthesis (based upon the trkB nucleic acid sequences of the invention), the problem of limited quantities of trkB has been obviated.

To further improve the likelihood of producing an anti-trkB immune response, the amino acid sequence of trkB may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphiphilic helix, amphiphilic sheet, and secondary structure of trkB. Alternatively, the deduced amino acid sequences of trkB from different species could be compared, and relatively non-homologous regions identified; these non-homologous regions would be more likely to be immunogenic across various species.

For preparation of monoclonal antibodies directed toward trkB, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of trkB. For the production of antibody, various host animals can be immunized by injection with trkB protein, or a fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a trkB epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules. Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

The abovementioned probes may be used experimentally to identify cells or tissues which hitherto had not been shown to express trkB. Furthermore, these methods may be used to identify the expression of trkB by aberrant tissues, such as malignancies. In additional embodiments, these methods may be used diagnostically to compare the expression of trkB in cells, fluids, or tissue from a patient suffering from a disorder with comparable cells, fluid, or tissue from a healthy person. Fluid is construed to refer to any body fluid, but particularly blood or cerebrospinal fluid. A difference in the levels of expression of trkB in the patient compared to a healthy person may indicate that the patient's disorder may be primarily or secondarily related to trkB metabolism. An increase in levels of trkB, for example, could either indicate that the patient's disorder is associated with an increased sensitivity to normal levels of neurotrophin or, alternatively, may suggest that the patient's neurotrophin levels are low such that the number of receptors is increased by way of compensation. These etiologies may be distinguished from one another by administering neurotrophin to the patient. If his condition worsens, he may suffer from neurotrophin hypersensitivity; if it improves, he may be suffering from a neurotrophin deficiency. Neurotrophin or neurotrophin antagonist-based therapeutic regimens may be chosen accordingly. Differences in expression can be detected at the protein and/or RNA level; i.e. by measuring amounts of trkB protein or trkB RNA in a patient relative to those amounts in healthy persons.

The abovementioned probes may also be used to select neurotrophin-responsive cells for use in assay systems, as described above, or in U.S. application Ser. No. 07/532,285 filed Jun. 1, 1990 (incorporated by reference herein, or according to standard methods of cell selection or cell sorting.

5.4. THERAPEUTIC APPLICATIONS

The present invention also provides for methods of treating a patient suffering from a neurological disorder comprising treating the patient with an effective amount of trkB protein, peptide fragment, or derivative thereof capable of binding to a neurotrophin. Therapeutic methods comprising administering trkB, trkB agonists, trkB antagonists (which compete with endogenous neurotrophin), or anti-trkB antibodies are within the scope of the present invention.

The present invention also provides for pharmaceutical compositions comprising trkB protein, peptide fragment, or derivative in a suitable pharmacologic carrier.

The trkB protein, peptide fragment, or derivative may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

As our understanding of neurodegenerative disease/neurotrauma becomes clearer, it may become apparent that it would be beneficial to decrease the trophic effect of endogenous neurotrophin. Therefore, in areas of nervous system trauma, it may be desirable to provide neurotrophin antagonists, including, but not limited to, soluble forms of trkB which may compete with endogenous cellular receptor for neurotrophin binding. Under such circumstances, it may be desirable to provide neurotrophin antagonist locally at the injury site rather than systemically. Use of a trkB providing implant may be desirable.

Alternatively, certain conditions may benefit from an increase in neurotrophin responsiveness. It may therefore be beneficial to increase the number or binding affinity of trkBs in patients suffering from such conditions. This could be achieved through gene therapy. Selective expression of recombinant trkB in appropriate cells could be achieved using trkB genes controlled by tissue specific or inducible promoters or by producing localized infection with replication defective viruses carrying a recombinant trkB gene. Conditions which may benefit from increased sensitivity to neurotrophin include particularly but are not limited to motorneuron disorders including amyotrophic lateral sclerosis, Werdnig-Hoffmann disease, chronic proximal spinal muscular atrophy, and Guillain-Barre syndrome. Such treatment may also be used for treatment of neurological disorders associated with diabetes, Parkinson's disease, Alzheimer's disease, and Huntington's chorea.

5.5. SYSTEMS FOR THE ASSAY AND DISCOVERY OF AGENTS THAT ACT ON RECEPTOR TYROSINE KINASES

The present invention also provides for systems that may be generally used in both the assay of pre-defined agents, as well as the discovery of novel agents, that act on receptor tyrosine kinases. In a related aspect of this invention, the same system can be used to discover unknown receptors that mediate responses to known factors. Once a particular receptor/ligand system is defined (as is done here with trkB and BDNF/NT-3), a variety of additional specific assay systems can be utilized, as detailed in other sections supra.

The present invention reveals that a receptor tyrosine kinase, when introduced into cells that do not normally express this receptor, allows these cells to exhibit profound and easily distinguishable responses to a ligand which binds this receptor. The present invention reveals that the type of response elicited depends on the cell utilized, and not the specific receptor introduced into the cell. Thus, the trkB receptor in PC12 pheochromocytoma cells results in BDNF/NT-3 dependent differentiation, whereas the same receptor in fibroblasts mediates both survival and proliferation in response to either BDNF or NT-3. Appropriate cell lines can be chosen to yield a response of the greatest utility for the assay, as well as discovery of, agents that can act on tyrosine kinase receptors. "Agents" refers to any molecule(s), including but not limited to peptide and non-peptide molecules, that will act in systems to be described in a receptor specific manner. One of the more useful systems to be exploited involves the introduction of the desired receptor (e.g. trkB) into a fibroblast cell line (e.g., the particular clone of NIH3T3 cells to be described below, section 7); thus such a receptor which does not normally mediate proliferative responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor.

Such systems are not limited to the assay of known ligands for known receptors, but can also be utilized to identify novel agents that might act on these or (or any other) receptors. For example, both the cell line bearing the introduced receptor as well as the parental cell line without the receptor can be exposed to any potential source of an agent that might work through the receptor; any specific effects (e.g. on cell survival or proliferation) on the cell line bearing the receptor can be used to identify sources of agents acting on that receptor, and to eventually purify such an agent.

Receptors also need not be limited to those for which a known ligand exists. In fact, this system may allow for the identification of ligands for "orphan" receptors so named because they have no known ligand. Thus, fibroblasts expressing trkB could have been used in such systems in order to identify and eventually purify the ligands (e.g. BDNF and NT-3) that normally activate trkB; they can now be used to identify additional such ligands or other agents (e.g. non-peptide molecules) that could act on these cells. Sources for "agents" could include extracts from a variety of tissues and organisms, or supernatants from cells transfected with genomic DNA or cDNA expression libraries. In a particular embodiment of this invention, fibroblasts expressing an introduced receptor for which a ligand is desired could be transfected with cDNA expression libraries derived from a potential source of such a ligand; cells which survive and form colonies in defined media lacking fibroblast growth facts (Zhan and Goldfarb, 1986, Mol. Cell. Biol., Vol. 6, pp. 3541–3544) would presumably now be making a growth factor that overcomes their normal requirements via an autocrine loop. To prove that this growth factor is working on the receptor of interest, supernatants harvested from these cells could now be assayed on the parental cell lines to prove that it only has actions on the parental cell line expressing this receptor; the transfected piece of DNA encoding the novel activity desired could then be isolated using traditional means.

A reciprocal approach could be used to molecularly clone a receptor for an "orphan" factor (for example, a neurotrophic protein for which no receptor has been isolated). Fibroblasts exposed to this factor normally would not respond, but if transfected with a cDNA expression library prepared from cells thought to be expressing this receptor, occasional transfectants would arise which now express this receptor and should now respond to this factor in an autocrine fashion. Powerful selection mechanisms, such as the ability to form colonies in defined media in the presence of the "orphan" factor, should identify transfectants that express the receptor of interest; the gene encoding this receptor could then be isolated by traditional means.

6. EXAMPLE: TRKB ENCODES A FUNCTIONAL RECEPTOR FOR BDNF AND NT-3 BUT NOT NGF

6.1. MATERIALS AND METHODS

6.1.1. CELL CULTURE, NEUROTROPHINS, AND IODINATION OF NEUROTROPHINS

COS-M5 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. PC12 cells were cultured in DMEM with 6% FBS and 6% horse serum, (P/S) and 2 mM glutamine on Costar tissue culture plates in an atmosphere of 7.5% $CO_2$.PC12 cells were obtained from Dr. L. A. Greene's laboratory were utilized in experiments depicted in FIG. 2, and PC12 cells obtained from Dr. E. M. Shooter's laboratory were utilized in experiments depicted in FIG. 5. The human neuroblastoma cell line, SH-SY5Y (obtained from June Biedler, Sloan-Kettering) was cultured in Eagle's minimal essential medium (EMEM) with 10% FBS, (P/S) and 2 mM glutamine.

Murine 2.5S NGF was obtained from Bioproducts for Science (Indianapolis, IN). Both human BDNF and NT-3 were produced in CHO cells and purified from CHO cell conditioned media to homogeneity as assessed by silver-stained polyacrylamide gels and amino acid sequence analysis. Purified neurotrophins (NGF, BDNF,, and NT-3) were all iodinated using the lactoperoxidase method as described in Hempstead et al., 1989, Science, 243: 373–375. Iodinated neurotrophins were separated from unincorporated $^{125}I$ by using a Centriflo CF50A filters (Amicon, Beverly, Mass.). Aggregates were removed using gel filtration (S200) column chromatography.

6.1.2. CLONING RAT trkB: MAMMALIAN EXPRESSION, CONSTRUCTS, AND TRANSIENT TRANSFECTIONS A full-length rat trkB cDNA clone was obtained by screening a rat brain cDNA library in the lambda ZAP2 vector (Stratagene) with rat trkB-specific oligonucleotides corresponding to the most 5' and 3' coding regions of trkB. Both the human LNGFR (Johnson et al., 1986, Cell 47: 545–554) and rat trkB cDNAs were subcloned into the mammalian expression vector, pCMX, to generate pCMX-LNGFR or pCMX-trkB respectively. pCMX-trkB(del) was generated by digesting the pCMX-trkB plasmid with ApaI (which cuts just after the trkB transmembrane domain) and Not1 (which cuts just after the trkB coding region in vector sequences), blunting these ends, and religating the plasmid; the trkB coding region generated includes all of the extracellular and transmembrane domains of trkB, but is lacking the C-terminal 320 amino acids.

COS-M5 cells were transiently transfected with either the pCMX-LNGFR, pCMX-trkB, or control vector (pCMX) by the DEAE-dextran transfection protocol. Briefly, COS-M5 cells were plated at a density of $1.5 \times 10^6$ cells per 100 mm plate 24 hours prior to transfection. For transfection, the cells were cultured in serum-free DMEM containing 400 µg/ml of DEAE-dextran, 1 µM chloroquin, 2 mM glutamine, 20 µg/ml insulin, 5 µg/ml transferrin, 33 nM sodium selenite, and 5 µg of the appropriate DNA for 3 hours and 15 minutes at 37° C. in an atmosphere of 5% CO2. The transfection media was aspirated and replaced with phosphate-buffered saline with 10% DMSO for 2 min. Following this DMSO "shock", the COS-M5 cells were placed into DMEM with 10% FBS, 1% each of penicillin and streptomycin, and 2 mM glutamine for 48 hours.

PC12 cells were transiently transfected by electroporation. Briefly, the cells were rinsed prior to transfection in ice-cold Dulbecco's phosphate-buffered saline (calcium and magnesium-free) containing 2 mg/ml glucose and then resuspended in the same buffer at a density of $1.5 \times 10^7$ cells per ml containing 40 µg of the appropriate DNA. PC12 cells were transfected with either pCMX, pCMX-trkB or the pT24-ras plasmid (Yancopoulos et al., 1985, Proc. Natl. Acad. Sci. USA., 82: 5455–5459). The cell mixture was incubated on ice for 10 min. and then quickly brought to room temperature and electroporated in a total volume of 1 ml at 1150 V/cm and 500 uF. Electroporated cells were incubated on ice for 30 minutes prior to plating in DMEM with 6% FBS and 6% horse serum with 1% each of penicillin and streptomycin and 2 mM glutamine; cells were plated on Costar plastic in the absence of any pre-coating. 48 hours after transfection, the cells were treated with 100 ng/ml of neurotrophin or BSA (see Legend of FIG. 5) and neurite outgrowth was scored 48 hours later.

6.1.3. CHEMICAL CROSS-LINKING

Cells were harvested in phosphate-buffered saline containing 1 mM EDTA, 1 mg/ml glucose and 25 mM HEPES (PBS-versene) and resuspended at an appropriate density (generally $1 \times 10^6$ cells per ml) in ice-cold binding buffer A (PBS containing 1 mg/ml each of BSA and glucose). pCMX-trkB or pCMX vector transfected COS-M5 cells ($4 \times 10^5$ cells) were incubated on ice with $^{125}$I-labeled neurotrophins (final concentration estimated to be between 0.1 and 0.25 nM) for 90 minutes in the absence or presence of unlabeled NGF, BDNF or NT-3 (see FIGS. 1 and 3). The chemical cross-linker DSS (Pierce, Rockford, Ill.) was used following conditions described in Meakin and Shooter, 1991, Neuron 6: 153–163. The cross-linking reaction was terminated after 90 minutes and quenched with 12 ml of 50 mM Tris buffer containing 160 mM NaCl. Cells were centrifuged at $300 \times$ g for 5 minutes and then washed twice with 12 ml of buffer A. Pelleted cells were solubilized in SDS containing 2% of 2-mercaptoethanol, boiled for 5 minutes; radiolabeled cross-linked proteins were resolved on 7% polyacrylamide gels and visualized by autoradiography after exposure of the dried gel to Kodak X-Omat film at −70° C.

6.1.4. $^{125}$I-NT-3 COMPETITION BINDING ASSAYS

Binding of $^{125}$I-NT-3 to COS-M5 cells transfected with either pCMX-LNGFR, pCMX-trkB or control vector (pCMX) was assessed on cells in suspension. Cells were harvested in PBS-versene and then resuspended in binding buffer A as described above for chemical cross-linking. Cells were incubated with $^{125}$I-NT-3 (estimated between 0.1 and 0.25 nM) in the absence or presence of increasing concentrations of unlabeled NT-3, BDNF, or NGF ranging from 0.3 to 30 nM for NGF and between 1 and 100 nM for BDNF and NT-3 (see FIG. 4C and D). The binding reactions were carried out for 90 minutes on ice. Free $^{125}$I was separated from bound $^{125}$I by quickly centrifuging (30 second spin) the reaction mixture through a sucrose gradient formed in a long-tip microcentrifuge tube. The tubes were immediately frozen in a dry-ice/ethanol bath. The bottom of the reaction tube was cut and then counted in a gamma counter.

6.1.5. RNA ISOLATION AND NORTHERN BLOTTING ANALYSIS

Total cellular RNA isolated from SH-SY5Y and treated or untreated PC12 cells was fractionated on 1% formaldehyde agarose gels, transferred to nylon membranes and hybridized to a $^{32}$P-labeled v-fos probe or a $^{32}$P-labeled c-jun probe as previously described (Squinto et al., 1990, Neuron 25, 757–766); probings for trkB expression were performed using a $^{32}$P-labeled rat trkB probe spanning a region encoding the intra-cytoplasmic tyrosine kinase domain.

6.2. RESULTS

6.2.1. ALL THREE NEUROTROPHINS BIND TO THE LNGFR BUT BDNF AND NT-3 DO NOT ACT VIA THE HNGFR

To determine whether NT-3, like NGF and BDNF (Rodriguez-Tebar, 1990, Neuron, 4: 487–492), could also bind to the LNGFR, we examined all three neurotrophins for their ability to be chemically cross-linked to the LNGFR protein expressed transiently in COS cells. Each of the three radiolabeled neurotrophins could be specifically cross-linked to a species of the molecular weight expected for the LNGFR (FIG. 1B cross-linked complex reported to be approximately 100 kb by Hosang and Shooter, J. Biol. Chem. 260: 655–662). The cross-linked product was not observed on COS cells that were not expressing the LNGFR protein (FIG. 1A). Furthermore, as expected for specific binding the appearance of the cross-linked products could be competed effectively by an excess of the corresponding unlabeled neurotrophin (FIG. 1B). Competable cross-linking to a polypeptide of the correct size was also observed in a cell line, A875 melanoma, known to stably express large amounts of the LNGFR (FIG. 1C).

Having established that all three neurotrophins bind to the LNGFR protein, we assessed the ability of BDNF and NT-3 to function via low or high affinity NGF receptors. The PC12 cell line, which expresses both classes of NGF receptor, displays prominent responses including both neurite outgrowth and the transcriptional induction of a set of so-called "immediate early genes" in response to NGF (Greene and Tischler, 1976, Proc. Natl. Acad. Sci. U.S.A., 73: 2424–2428; Greenberg et al., 1985, J.Biol. Chem. 260: 14101–14110, see FIG. 2A, B). However, when PC12 cells were incubated with BDNF or NT-3 at concentrations either below or exceeding that known to be saturating for responses to NGF, we observed neither morphological changes (under conditions optimal for neurite outgrowth, see below) nor the induction of immediate early gene expression FIG. 2A, 2B. This implies that neither low nor high affinity NGF receptors suffice for functional responses to BDNF and NT-3 and that such responses require at least one receptor component not normally found on PC12 cells.

6.2.2. BDNF AND NT-3, BUT NOT NGF, BIND TO FULL-LENGTH AND TRUNCATED FORMS OF TRKB

TrkB is not expressed in PC12 cells (Kaplan et al., 1991, Nature 350: 158–160); cell lines expressing trkB have not been described. A full-length trkB cDNA was isolated and transiently expressed in COS cells, on which cross-linking experiments were carried out with radioiodinated neurotrophins. As shown in FIG. 3A both BDNF and NT-3, but not NGF, could be cross-linked to a polypeptide of approximately the expected size for the trkB gene product; some heterogeneity in the size of this cross-linked species was observed, as has been previously reported for the HNGFR cross-linked to NGF (Meakin and Shooter, 1991, Neuron 6: 153–163). Cross-linking of labeled BDNF or NT-3 to the presumptive trkB gene product was not observed in the presence of excess unlabeled homologous ligand (FIG. 3A, lanes labeled "+"). To verify that the protein cross-linked to BDNF or NT-3 actually corresponds to the trkB gene product, and to determine whether certain truncated forms of the protein are capable of binding ligands, a trkB deletion mutant lacking the intracytoplasmic protein-tyrosine kinase domain was constructed and expressed in COS cells. As illustrated in FIG. 3B, radiolabeled ligand (in this case NT-3) was cross-linked efficiently to a surface component of cells expressing the truncated trkB product; furthermore, the marked shift in mobility (corresponding to about 35 kD) observed between the cross-linked species obtained with full-length or truncated trkB proteins agreed well with the known size of the deletion.

6.2.3. BDNF AND NT-3, BUT NOT NGF, COMPETE FOR BINDING TO TRKB AND DISPLAY HIGHER AFFINITY BINDING TO TRKB THAN THEY DO TO LNGFR

Figure 4A:
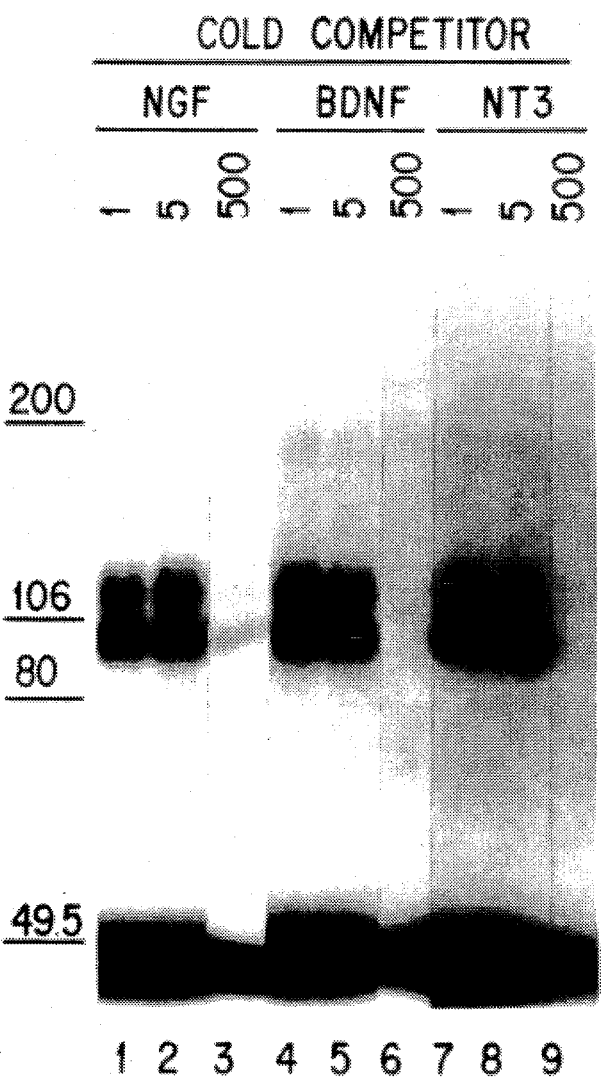

The specificity and relative affinity of binding of the neurotrophins to the LNGFR and to trkB was compared in competition assays. Each of the three unlabeled neurotrophins were effectively able to specifically block the cross-linking of radiolabeled NT-3 to the LNGFR expressed in COS cells when present at 500 nM levels but not at 1–5 nM levels (FIG. 4A). Consistent with these results, the binding of radiolabeled NT-3 to the LNGFR expressed on COS cells was completed similarly by each of the three unlabeled neurotrophins (FIG. 4C); the competition curves suggest dissociation constants in the nanomolar range for all three neurotrophins, extending previous observations for NGF and BDNF (Rodriguez-Tebar et al., 1990, Neuron 4: 487–492).

Figure 4B:
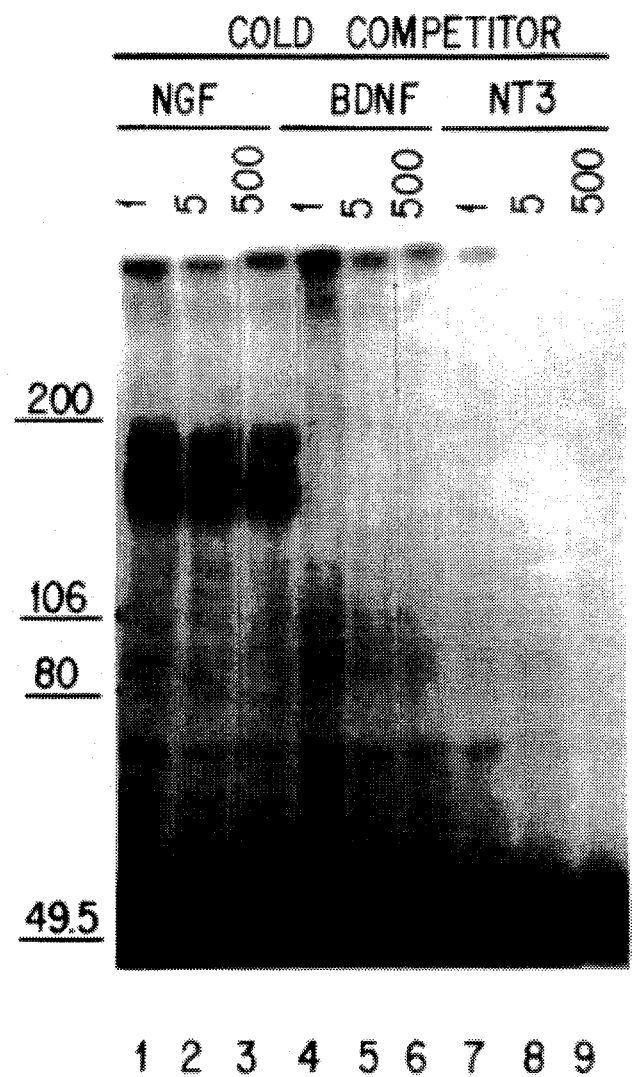
Figure 4D:
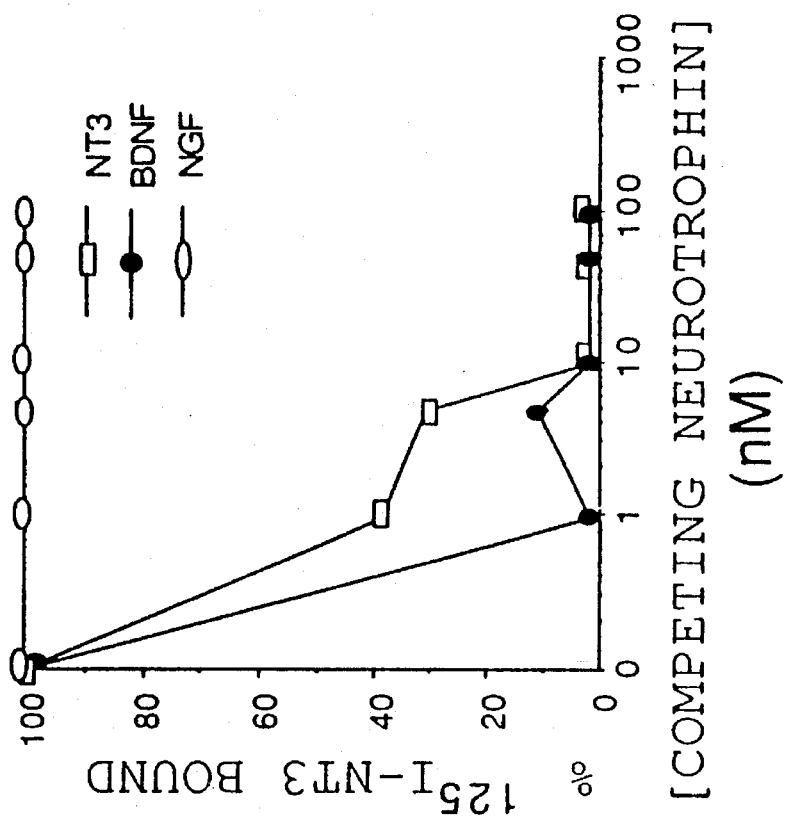
Figure 4C:
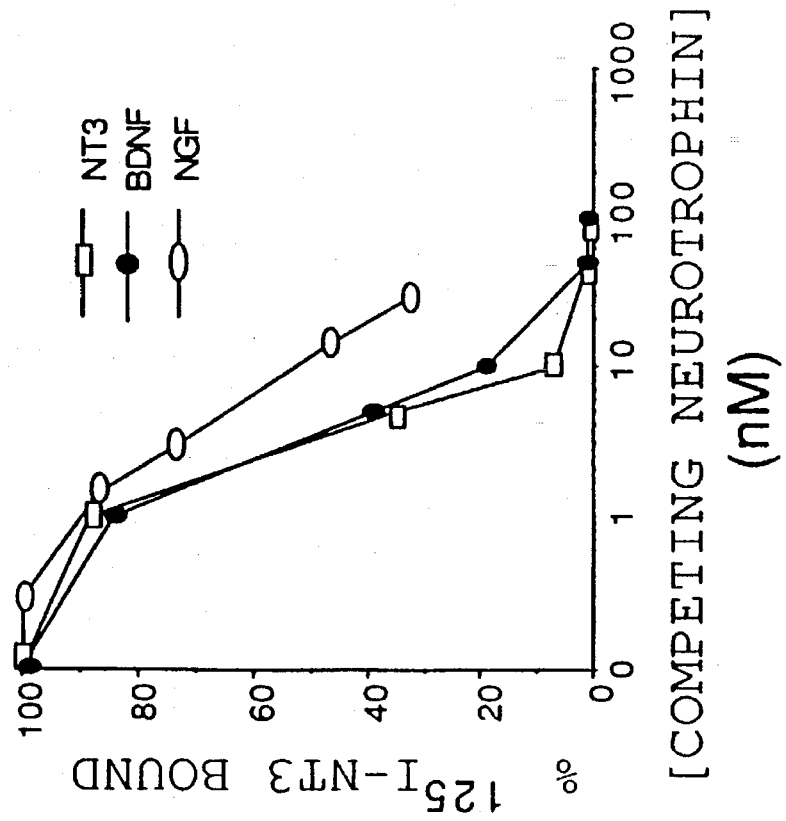

In contrast to the rather high levels of unlabeled ligands required to specifically block binding to the LNGFR, much lower levels of unlabeled BDNF and NT-3 effectively prevented binding of radiolabeled NT-3 to trkB as assayed either by cross-linking (FIG. 4B) or direct binding analysis (FIG. 4D). NGF, even at 500–1000 fold molar excess, did not compete for binding of radiolabeled NT-3 to trkB in either assay (FIG. 4B, 4D). Because the amounts of unlabeled BDNF and NT-3 required to completely inhibit the binding of radiolabeled NT-3 to trkB were 10 to 100-fold lower than those necessary to block binding of NT-3 to the LNGFR, our data suggest that trkB displays considerably higher affinity for both BDNF and NT-3 than does the LNGFR.

6.2.4. TRKB MEDIATES NEURITE OUTGROWTH IN RESPONSE TO BOTH BDNF AND NT-3 IN PC12 CELLS

Figure 5A:
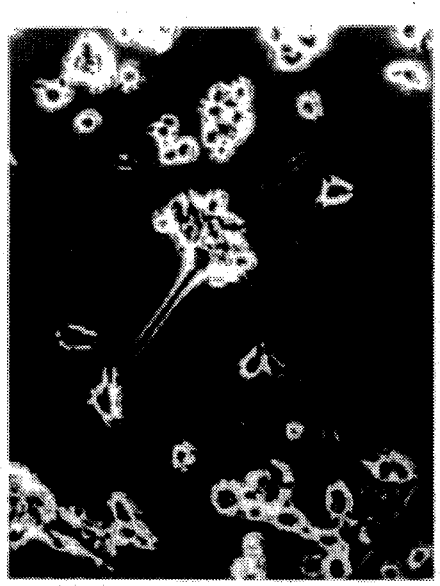
Figure 5B:
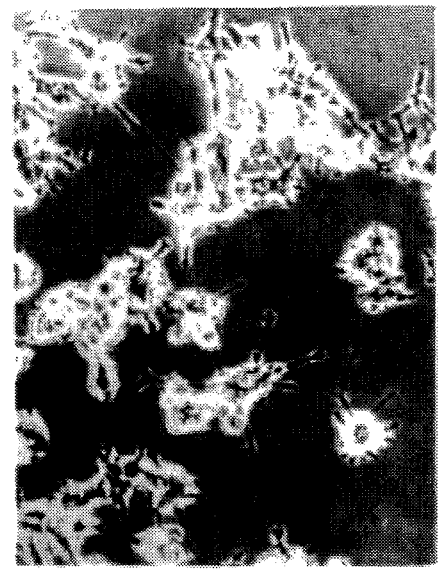
Figure 5C:
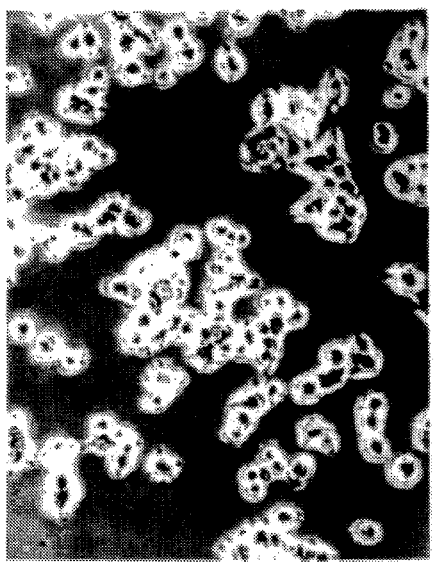
Figure 5D:
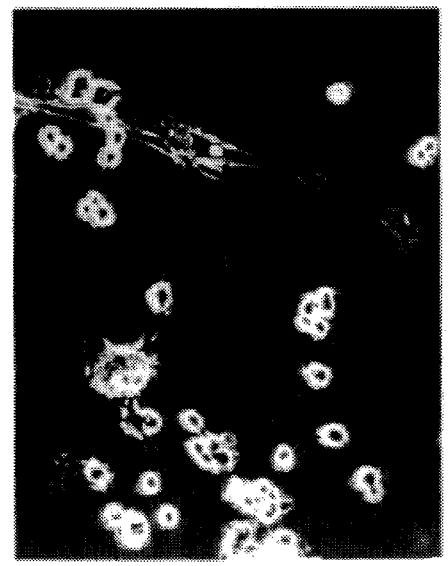
Figure 5E:
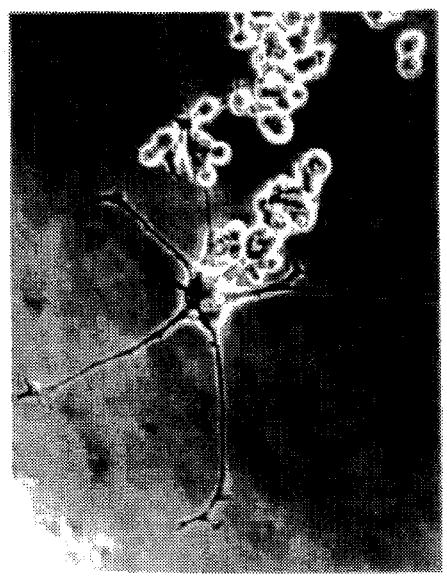

PC12 cells display a characteristic morphological response, neurite extension, indicative of differentiation to a more mature neuronal phenotype when exposed to NGF. As demonstrated above, these cells do not respond to either BDNF or NT-3. To test whether trkB could mediate a biologically relevant response to BDNF or NT-3, PC12 cells were transiently transfected with a trkB expression vector (pCMX-trkB) and incubated with each of the neurotrophins. In order to minimize background, the transfected cells were cultured on standard tissue culture plastic rather than either collagen-coated or Primaria surfaces; under these conditions which are suboptimal for neurite extension (Greene et al., 1987, Meth. Enzymol., 147: 207–216; Chen et al., 1990, Cell Growth Diff. 1:79–85), NGF induced rather short neurites from control PC12 cells as well as from the trk-B-transfected cells (FIG. 5B). No cells with neurites were seen in the trkB-transfected cultures in the absence of added neurotrophic factor (FIG. 5C). However, many cells in the trkB-transfected PC12 cultures displayed robust neuritic outgrowth in response to either NT-3 or BDNF (FIG. 5D, E); no cells with neurites were seen in PC12 cells transiently transfected with control vectors and treated with BDNF or NT-3. As a positive control to assess transfection efficiency, the PC12 cells were transfected with an activated H-ras gene, which has been shown to induce ligand-independent differentiation of PC12 cells. The number of differentiated cells seen in the ras-transfected cultures indicates the number of transiently transfected PC12 cells in the cultures. Since the number of differentiated cells observed following BDNF treatment of pCMX-trkB transfected PC12 cells is comparable with the number of differentiated cells found in the ras-transfected populations (FIG. 5A, E), our data suggests that every PC12 cell expressing trkB can respond to BDNF while, however, a smaller subset of trkB expressing PC12 cells responded to NT-3 as measured by neurite outgrowth (FIG. 5D); more careful dose-response studies will be required to evaluate the apparent difference between BDNF and NT-3 in this assay. As depicted in FIG. 5, it was striking that the extensive neuritic outgrowth seen in ras-transfected PC12 cells or in pCMX-trkB-transfected PC12 cells subjected to BDNF or NT-3 was qualitatively different than the blunted neuritic outgrowth normally seen in response to NGF under these culture conditions.

6.2.5. SH-SH5Y HUMAN NEUROBLASTOMA CELLS RESPOND TO BDNF, BUT NOT NT-3, AND DO NOT EXPRESS TRKB: EVIDENCE FOR ANOTHER NEUROTROPHIN RECEPTOR

We have used the induction of immediate early gene expression as an assay (Squinto et al., 1990, Neuron 5:757–766) to search for neuronal tumor cell lines responsive to BDNF, NT-3 and NGF. One such line (SH-SY5Y) was found to express c-fos mRNA in response to both NGF (as previously described) and BDNF, but not NT-3 (FIG. 6A). Further studies have verified that BDNF, but not NT-3, has additional functional effects on SH-HY5Y; for example, BDNF protects these cells from oxidative insults. Although this cell line has been shown to express low levels of both high and low affinity NGF receptors (Chen et al., 1990, Cell Growth Diff., 1:79–85) and detectable levels of trkAmRNA, it did not express detectable levels of trkBmRNA (FIG. 6B). The apparent lack of trkB expression in a BDNF-responsive cell line, together with its failure to respond to NT-3, leads us to predict that either there are additional modulators of the LNGFR or trkA which confer BDNF responsiveness, or that yet another functional neurotrophin receptor exists which has discrete specificity for BDNF.

6.3. DISCUSSION

We conclude that trkB encodes an essential component of a functional receptor for BDNF and NT-3, but not for the third neurotrophin family member, NGF. Recent reports indicate that the trkA proto-oncogene, the closest known relative of trkB, similarly encodes an essential component for a high affinity receptor which binds NGF (Kaplan et al., 1991, Nature, 350: 158–160; Klein et al., 1991, EMBO J. 8: 3701–3709). Our observations that normal PC12 cells do not respond to BDNF or NT-3 imply that trkA, which is expressed in PC12 cells, is uniquely activated by only one known member of the neurotrophin family, NGF.

We find that BDNF and NT-3 bind to trkB in the absence of the LNGFR, and that this binding is of higher affinity than their binding to the LNGFR. Similarly, Klein et al. (1991, Cell 65:189–197) report that NGF can bind to trkA with high affinity in cells that do not express the LNGFR. The function of the LNGFR remains unclear. We extend previous findings (Rodriguez-Tebar et al., 1990, Neuron 4: 487–492) by demonstrating that all three neurotrophins bind to the LNGFR with approximately equal, albeit relatively low, affinity; the conservation of this property suggests a significant biological role. It remains possible that the LNGFR modulates the binding of each of the neurotrophins to its appropriate trk receptor. Alternatively, the LNGFR may mediate signal transduction via an independent pathway, or it may not be directly involved in initiating signal transduction. For example it may act to localize, concentrate or trap the neurotrophins on the surface of LNGFR-expressing cells. In this regard it is of interest that neuronal supporting cells (such as Schwann cells) that do not respond to NGF express the LNGFR and up-regulate it in response to injury (Johnson et al., 1988, TINS 11: 299–304), perhaps providing a fixed matrix or path for the concentration and presentation of neurotrophins to regenerating neurons. Alternatively, the LNGFR may act as a "clearance" receptor that reduces free or circulating levels of the neurotrophins; the LNGFR is widely distributed both in the CNS and in the periphery (Maisonpierre et al., 1990, Neuron 5: 501–509), and secreted forms of the LNGFR (DiStefano and Johnson, 1988, Proc. Natl. Acad., Sci. USA, 85: 270–274) may aid in such clearance mechanisms In regard to non-signalling roles for the LNGFR, related mechanisms specific for BDNF and NT-3 can be proposed based on the presence of truncated forms of trkB. The co-localization of BDNF and truncated trkB transcripts outside of the nervous system (most prominently in lung and skeletal muscle) raises intriguing questions concerning the role of BDNF, trkB and other potential BDNF receptors in non-neural tissues.

The fact that BDNF and NT-3 share a functional receptor, trkB, is consistent with our previous suggestions that the distributions and overlapping neuronal specificities of BDNF and NT-3 particularly link the roles of these two neurotrophins, at least in the central nervous system. During the maturation of different brain regions marked by decreasing NT-3 levels and increasing BDNF levels, the expression of trkB remains relatively constant. However, the identification of a cell line which responds to BDNF but not NT-3 and does not detectably express trkB strongly suggests that these two neurotrophins are not entirely interchangeable, and that there may exist additional receptors or modulatory components, which allow for distinct responses to either BDNF or NT-3. Such modulation may explain, for example, the differing effects of NT-3 and BDNF on PC12 cells transfected with trkB (see above) or on sympathetic neurons (Maisonpeirre et al., 1990, Science, 247: 1446–1451). Sympathetic neurons are known to express trkB, although the available in situ hybridization data do not distinguish between the presence of functional or non-functional trkB transcripts in these neurons (Klein et al., 1989, EMBO J. 8: 3701–3709). An evolutionary comparison of BDNF and NT-3 lead us to predict that these two neurotrophins were strictly conserved to maintain their specific interactions with multiple receptors. Although NGF is well conserved evolutionarily compared to most secreted factors, it does not display the striking conservation that BDNF and NT-3 do, perhaps suggesting that it does not interact with as many receptors as the other two known neurotrophins. Our findings place the neurotrophins in the growing class of receptor/ligand systems in which multiple receptors each bind to several different related ligands (reviewed in Cross and Dexter, 1991, Cell, 64: 271–280).

The binding and activation of receptor tyrosine kinases by the neurotrophins reveals that these factors utilize signalling pathways very similar to those activated by mitogenic growth factors. This finding is consistent with recent data that neurotrophic factors can act as mitogens in certain contexts (e.g. Cattaneo and McKay, 1990, Nature, 347: 762–765), but also indicates that signals which initiate the activation of receptor tyrosine kinases normally integrate into non-mitogenic transduction pathways in neurons. Despite differences in ultimate sequelae (i.e. mitogenesis vs. survival or differentiation), at least some of the early intermediates in tyrosine kinase signalling cascades, such as the ERK family of protein kinases, are similarly activated in both neuronal and non-neuronal cells. Other examples in which activation of receptor-like tryosine kinases in neuronal cells leads to non-mitogenic sequelae include the Drosophila sevenless protein, where activation via a non-diffusable ligand is required for the differentiation of photoreceptor cells (Basler et al., 1991, Cell, 64: 1069–1081).

7. EXAMPLE: NIH 3T3-CELL NEUROTROPHIN ASSAY SYSTEM

7.1. MATERIALS AND METHODS

7.1.1. PREPARATION OF CELL LINES

An NIH 3T3 fibroblast cell line was obtained from Dr. Mitch Goldfarb (Columbia University). This clone of NIH 3T3 cells displays a growth-factor dependence (i.e. FGF and PDGF) for survival and proliferation in serum-free media (Zhan and Goldfarb, 1986, Mol. Cell. Biol. 6:3541–3544).

7.1.1.1. INSERTING THE HUMAN LOW AFFINITY GROWTH FACTOR RECEPTOR INTO NIH 3T3 CELLS

First, the human LNGFR (Low Affinity Nerve Growth Factor Receptor) was inserted into a retroviral vector, derived from the M-MuLV retrovirus. This construct was stably transfected by $CaPO_4$ into a helper-free packaging line called AM12, and was cotransfected with a neomycin gene to permit selection of successfully transfected cells. Neomycin resistant transfectants were selected by growing the cells in the presence of the neomycin drug G418. These G418-survivors were next assayed for the presence of the LNGFR by direct binding to radiolabeled NGF. The cells were also checked to make sure that they did not contain active virus.

From these procedures, several subclones of NIH 3T3 cells were derived which tested positive for the presence of the LNGFR, one of which is designated (NIH 3T3 +LNGFR)

7.1.2. INSERTING THE RAT TrkB RECEPTOR INTO NIH 3T3 CELLS

NIH 3T3 cells were transfected by $CaPO_4$ with 5 micrograms of a construct containing the rat TrkB gene inserted into a M-MuLV-promoter-based expression vector. One microgram of a hygromycin vector was also co-transfected, and 15 micrograms of human liver genomic DNA was added to the transfection, as carrier. The cells were allowed to recover for 48 hours after the transfection, and were then grown in the presence of 250 μg/ml of hygromycin, to select for hygromycin-resistant cells. The cells were grown for two weeks in the presence of hygromycin, and resistant colonies were then pooled. We refer to this pool of cells as (MIH 3T3+trkB). Similar transfections were carried out to introduce trkB into NIH 3T3 cells already expressing the LNGFR, and pools resulting from the CSC transfections were designated NIH 3T3 HLNGFR+trkB).

7.2. RESULTS: ESTABLISHING THE LIGANDS FOR TrkB, USING THE DEFINED MEDIA ASSAY

One $\times 10^5$ of each (NIH 3T3+LNGFR), (NIH 3T3+trkB), and (NIH 3T3+LNGFR=trkB) cells were plated on each of six Nunc Tissue Culture plates coated with Poly-D-Lysine and human fibronectin. The cells were allowed to grow in DMEM +10% Bovine Calf Serum for four hours, to allow them to bind to the plates. The serum-containing media was then aspirated, and the plates were washed 3 times with PBS(–) buffer, to remove all traces of serum.

The cells were then treated with either serum-free defined media or, as a control, DMEM plus 10% CS. The serum-free defined media is made in the following manner: A 3:1 mixture of DNEM+Hams F12 medium supplemented with 8 mM sodium bicarbonate, 15 mM HEPES, $4\times 10^{-6}$M $MnCl_2$, 3 mM histidine, to $10^{-5}$M ethanolamine was supplemented with:

1) 500 mg/liter linoleic acid/BSA from Sigma (Catalog Number L 8384)
2) 20 ml of an Insulin-Transferrin-Sodium Selenite Media Supplement (provided by Sigma, Catalog Number I-1884; resuspended in 50 ml of PBS(–).
3) Gentamicin, Penicillin and Streptomycin for antimicrobial prophylaxis
4) L-Glutamine (20 mM final concentration).

The six plates from each of the cell populations used were plated as follows:

Plate Number:

1) DMEM+10% Calf Serum+hygromycin
2) Defined Media with no (zero) growth factor
3) Defined Media with 100 ng/ml NT-3 (Regeneron Batch #910502)
4) Defined Media with 100 ng/ml BDNF (Regeneron Batch #01181)
5) Defined Media with 100 ng/ml NGF (Collaborative Research Lot #910639)
6) Defined Media with 10 ng/ml basic FGF (Amgen)

The plates were allowed to grow for five days, replacing the media and growth factors every 48 hours.

After four days it was clear by observation (see FIG. 7) that the (NIH 3T3+LNGFR) cells, like control NIH 3T3 cells, survived and proliferated only in the presence of serum (not shown) or FGF (FIG. 7). However, both (NIH 3T3+LNGFR+trkB) and (NIH 3T3+trkB) also survived and proliferated in defined media supplemented with either BDNF or NT-3, but not NGF. Thus, these data confirm the observation (supra) that trkB serves as a functional receptor for both BDNF and NT-3, but not NGF. Furthermore, it establishes that the LNGFR is not essential for this ligand-dependent trkB mediated response, at least in certain cell types. In addition, the failure of LNGFR to confer neurotrophin dependent growth demonstrates that not all neurotrophin binding molecules can confer responsiveness when expressed in a recipient cell. To further demonstrate that BDNF and NT-3 elicit survival/proliferative responses via activation of trkB tyrosine kinase activity, we analyzed (NIH 3T3+LNGFR) and (NIH 3T3+LNGFR+trkB) for changes in their tyrosinephosphorylation state. In response to BDNF only the (NIH 3T3+LNGFR+trkB) displays an increase in tyrosine phosphorylation of a protein corresponding in size to trkB. Thus, NIH 373 cells expressing trkB display ligand-dependent tyrosine phosphorylation.

The construction of 3T3 cell lines whose survival and proliferation is dependent upon BDNF or NT-3 affords a very powerful selection modality. These cells can efficiently be used to provide assay systems to precisely quantitate levels of BDNF or NT-3 in samples. Furthermore, they can be used as assay systems to identify and quantify novel neurotrophin-like activities. One could use such assays as screens for antagonists of neurotrophin activity based on inhibition of BDNF/NT-3 dependent survival or proliferation. The specificity of these agonists/antagonists could be determined by judicious use of the cells. For example, agonists should only act on trkB expressing cells, not the parental cells, while specific antagonists would have to act only on BDNF or NT-3 stimulated trkB-expressing cells, and not the same cells subjected to FGF treatment. It should be noted that these activities need not correlate with binding to trkB because they might act anywhere in the specific trkB mediated signal transduction pathway.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2463 base pairs
( B ) TYPE: nucleic acid
( C ) STRANDEDNESS: unknown
( D ) TOPOLOGY: unknown ( i i ) MOLECULE TYPE: cDNA ( i x ) FEATURE:
    ( A ) NAME/KEY: CDS
    ( B ) LOCATION: 1..2463

( x i ) SEQUENCE DESCRIPTION: SEQ ID NO:1:

```
ATG TCG CCC TGG CTG AAG TGG CAT GGA CCC GCC ATG GCG CGG CTC TGG        48
Met Ser Pro Trp Leu Lys Trp His Gly Pro Ala Met Ala Arg Leu Trp
 1               5                  10                  15

GGC TTA TGC CTG CTG GTC TTG GGC TTC TGG AGG GCC TCT CTC GCC TGC        96
Gly Leu Cys Leu Leu Val Leu Gly Phe Trp Arg Ala Ser Leu Ala Cys
             20                  25                  30

CCG ACG TCC TGC AAA TGC AGT TCC GCT AGG ATT TGG TGT ACT GAG CCT       144
Pro Thr Ser Cys Lys Cys Ser Ser Ala Arg Ile Trp Cys Thr Glu Pro
         35                  40                  45

TCT CCA GGC ATC GTG GCA TTC CCG AGG TTG GAA CCT AAC AGC GTT GAC       192
Ser Pro Gly Ile Val Ala Phe Pro Arg Leu Glu Pro Asn Ser Val Asp
     50                  55                  60

CCG GAG AAC ATC ACG GAA ATT CTC ATT GCA AAC CAG AAA AGG CTA GAA       240
Pro Glu Asn Ile Thr Glu Ile Leu Ile Ala Asn Gln Lys Arg Leu Glu
 65                  70                  75                  80

ATC ATC AAT GAA GAT GAC GTT GAA GCT TAC GTG GGG CTG AGA AAC CTT       288
Ile Ile Asn Glu Asp Asp Val Glu Ala Tyr Val Gly Leu Arg Asn Leu
                 85                  90                  95

ACA ATT GTG GAT TCC GGC TTA AAG TTT GTG GCT TAC AAA GCG TTT CTG       336
Thr Ile Val Asp Ser Gly Leu Lys Phe Val Ala Tyr Lys Ala Phe Leu
            100                 105                 110

AAA AAC AGC AAC CTG CGG CAC ATA AAT TTC ACA CGA AAC AAG CTG ACG       384
Lys Asn Ser Asn Leu Arg His Ile Asn Phe Thr Arg Asn Lys Leu Thr
        115                 120                 125

AGT TTG TCC AGG AGA CAT TTC CGC CAC CTT GAC TTG TCT GAC CTG ATC       432
Ser Leu Ser Arg Arg His Phe Arg His Leu Asp Leu Ser Asp Leu Ile
    130                 135                 140

CTG ACG GGT AAT CCG TTC ACG TGC TCC TGC GAC ATC ATG TGG CTC AAG       480
Leu Thr Gly Asn Pro Phe Thr Cys Ser Cys Asp Ile Met Trp Leu Lys
145                 150                 155                 160

ACT CTC CAG GAG ACT AAA TCC AGC CCC GAC ACT CAG GAT TTG TAC TGC       528
Thr Leu Gln Glu Thr Lys Ser Ser Pro Asp Thr Gln Asp Leu Tyr Cys
                165                 170                 175

CTC AAT GAG AGC AGC AAG AAC ATG CCC CTG GCG AAC CTG CAG ATA CCC       576
Leu Asn Glu Ser Ser Lys Asn Met Pro Leu Ala Asn Leu Gln Ile Pro
            180                 185                 190

AAT TGT GGT CTG CCA TCT GCA CGT CTG GCT GCT CCT AAC CTC ACC GTG       624
Asn Cys Gly Leu Pro Ser Ala Arg Leu Ala Ala Pro Asn Leu Thr Val
        195                 200                 205

GAG GAA GGA AAG TCT GTG ACC CTT TCC TGC AGT GTG GGG GGT GAC CCA       672
Glu Glu Gly Lys Ser Val Thr Leu Ser Cys Ser Val Gly Gly Asp Pro
    210                 215                 220

CTC CCC ACC TTG TAC TGG GAC GTT GGG AAT TTG GTT TCC AAG CAC ATG       720
Leu Pro Thr Leu Tyr Trp Asp Val Gly Asn Leu Val Ser Lys His Met
225                 230                 235                 240

AAT GAA ACA AGC CAC ACA CAG GGC TCC TTA AGG ATA ACG AAC ATT TCA       768
Asn Glu Thr Ser His Thr Gln Gly Ser Leu Arg Ile Thr Asn Ile Ser
                245                 250                 255

TCT GAT GAC AGT GGA AAG CAA ATC TCT TGT GTG GCA GAA AAC CTT GTA       816
Ser Asp Asp Ser Gly Lys Gln Ile Ser Cys Val Ala Glu Asn Leu Val
            260                 265                 270

GGA GAA GAT CAA GAT TCT GTG AAC CTC ACT GTG CAT TTT GCG CCA ACT       864
Gly Glu Asp Gln Asp Ser Val Asn Leu Thr Val His Phe Ala Pro Thr
        275                 280                 285
```

| | | | | | | | | | | | | | | | | |
|---|---|---|---|---|---|---|---|---|---|---|---|---|---|---|---|---|
| ATC | ACG | TTT | CTC | GAG | TCT | CCA | ACC | TCA | GAT | CAC | CAC | TGG | TGC | ATT | CCA | 912 |
| Ile | Thr | Phe | Leu | Glu | Ser | Pro | Thr | Ser | Asp | His | His | Trp | Cys | Ile | Pro | |
| | 290 | | | | 295 | | | | | 300 | | | | | | |
| TTC | ACT | GTG | AGA | GGC | AAC | CCC | AAG | CCT | GCG | CTT | CAG | TGG | TTC | TAC | AAT | 960 |
| Phe | Thr | Val | Arg | Gly | Asn | Pro | Lys | Pro | Ala | Leu | Gln | Trp | Phe | Tyr | Asn | |
| 305 | | | | | 310 | | | | | 315 | | | | | 320 | |
| GGG | GCC | ATA | CTG | AAT | GAG | TCC | AAG | TAC | ATC | TGT | ACT | AAG | ATC | CAC | GTC | 1008 |
| Gly | Ala | Ile | Leu | Asn | Glu | Ser | Lys | Tyr | Ile | Cys | Thr | Lys | Ile | His | Val | |
| | | | | 325 | | | | | 330 | | | | | 335 | | |
| ACC | AAT | CAC | ACG | GAG | TAC | CAT | GGC | TGC | CTC | CAG | CTG | GAT | AAC | CCC | ACT | 1056 |
| Thr | Asn | His | Thr | Glu | Tyr | His | Gly | Cys | Leu | Gln | Leu | Asp | Asn | Pro | Thr | |
| | | | 340 | | | | | 345 | | | | | 350 | | | |
| CAT | ATG | AAT | AAC | GGA | GAC | TAC | ACC | CTG | ATG | GCC | AAG | AAC | GAG | TAT | GGG | 1104 |
| His | Met | Asn | Asn | Gly | Asp | Tyr | Thr | Leu | Met | Ala | Lys | Asn | Glu | Tyr | Gly | |
| | | 355 | | | | | 360 | | | | | 365 | | | | |
| AAG | GAT | GAG | AGA | CAG | ATC | TCC | GCT | CAC | TTC | ATG | GGC | CGG | CCT | GGA | GTC | 1152 |
| Lys | Asp | Glu | Arg | Gln | Ile | Ser | Ala | His | Phe | Met | Gly | Arg | Pro | Gly | Val | |
| | 370 | | | | | 375 | | | | | 380 | | | | | |
| GAC | TAC | GAG | ACA | AAC | CCA | AAT | TAC | CCT | GAA | GTC | CTC | TAT | GAA | GAC | TGG | 1200 |
| Asp | Tyr | Glu | Thr | Asn | Pro | Asn | Tyr | Pro | Glu | Val | Leu | Tyr | Glu | Asp | Trp | |
| 385 | | | | | 390 | | | | | 395 | | | | | 400 | |
| ACC | ACG | CCA | ACT | GAC | ATT | GGG | GAT | ACT | ACG | AAC | AAA | AGT | AAT | GAA | ATC | 1248 |
| Thr | Thr | Pro | Thr | Asp | Ile | Gly | Asp | Thr | Thr | Asn | Lys | Ser | Asn | Glu | Ile | |
| | | | | 405 | | | | | 410 | | | | | 415 | | |
| CCC | TCC | ACG | GAT | GTT | GCT | GAC | CAA | AGC | AAT | CGG | GAG | CAT | CTC | TCG | GTC | 1296 |
| Pro | Ser | Thr | Asp | Val | Ala | Asp | Gln | Ser | Asn | Arg | Glu | His | Leu | Ser | Val | |
| | | | 420 | | | | | 425 | | | | | 430 | | | |
| TAT | GCC | GTG | GTG | GTG | ATT | GCA | TCT | GTG | GTG | GGA | TTC | TGC | CTG | CTG | GTG | 1344 |
| Tyr | Ala | Val | Val | Val | Ile | Ala | Ser | Val | Val | Gly | Phe | Cys | Leu | Leu | Val | |
| | | 435 | | | | | 440 | | | | | 445 | | | | |
| ATG | TTG | CTC | CTG | CTC | AAG | TTG | GCG | AGA | CAT | TCC | AAG | TTT | GGC | ATG | AAA | 1392 |
| Met | Leu | Leu | Leu | Leu | Lys | Leu | Ala | Arg | His | Ser | Lys | Phe | Gly | Met | Lys | |
| | 450 | | | | | 455 | | | | | 460 | | | | | |
| GGC | CCA | GCT | TCG | GTC | ATC | AGC | AAC | GAT | GAT | GAC | TCT | GCC | AGC | CCC | CTC | 1440 |
| Gly | Pro | Ala | Ser | Val | Ile | Ser | Asn | Asp | Asp | Asp | Ser | Ala | Ser | Pro | Leu | |
| 465 | | | | | 470 | | | | | 475 | | | | | 480 | |
| CAC | CAC | ATC | TCC | AAT | GGG | AGT | AAC | ACT | CCA | TCT | TCT | TCG | GAG | GGC | GGT | 1488 |
| His | His | Ile | Ser | Asn | Gly | Ser | Asn | Thr | Pro | Ser | Ser | Ser | Glu | Gly | Gly | |
| | | | | 485 | | | | | 490 | | | | | 495 | | |
| CCC | GAC | GCT | GTC | ATT | ATT | GGA | ATG | ACC | AAG | ATT | CCT | GTT | ATT | GAA | AAC | 1536 |
| Pro | Asp | Ala | Val | Ile | Ile | Gly | Met | Thr | Lys | Ile | Pro | Val | Ile | Glu | Asn | |
| | | | 500 | | | | | 505 | | | | | 510 | | | |
| CCC | CAG | TAC | TTT | GGC | ATC | ACC | AAC | AGT | CAG | CTC | AAG | CCA | GAC | ACA | TTT | 1584 |
| Pro | Gln | Tyr | Phe | Gly | Ile | Thr | Asn | Ser | Gln | Leu | Lys | Pro | Asp | Thr | Phe | |
| | | 515 | | | | | 520 | | | | | 525 | | | | |
| GTT | CAG | CAC | ATC | AAG | AGA | CAC | AAC | ATC | GTT | CTG | AAG | AGG | GAA | CTT | GGG | 1632 |
| Val | Gln | His | Ile | Lys | Arg | His | Asn | Ile | Val | Leu | Lys | Arg | Glu | Leu | Gly | |
| | 530 | | | | | 535 | | | | | 540 | | | | | |
| GAA | GGA | GCC | TTC | GGG | AAA | GTT | TTC | CTT | GCC | GAG | TGC | TAC | AAC | CTC | TGC | 1680 |
| Glu | Gly | Ala | Phe | Gly | Lys | Val | Phe | Leu | Ala | Glu | Cys | Tyr | Asn | Leu | Cys | |
| 545 | | | | | 550 | | | | | 555 | | | | | 560 | |
| CCA | GAG | CAG | GAT | AAG | ATC | CTG | GTG | GCT | GTG | AAG | ACG | CTG | AAG | GAC | GCC | 1728 |
| Pro | Glu | Gln | Asp | Lys | Ile | Leu | Val | Ala | Val | Lys | Thr | Leu | Lys | Asp | Ala | |
| | | | | 565 | | | | | 570 | | | | | 575 | | |
| AGC | GAC | AAT | GCA | CGC | AAG | GAC | TTT | CAT | CGG | GAA | GCT | GAG | CTG | CTG | ACC | 1776 |
| Ser | Asp | Asn | Ala | Arg | Lys | Asp | Phe | His | Arg | Glu | Ala | Glu | Leu | Leu | Thr | |
| | | | 580 | | | | | 585 | | | | | 590 | | | |
| AAC | CTC | CAG | CAC | GAG | CAC | ATT | GTC | AAG | TTC | TAC | GGT | GTC | TGT | GTG | GAG | 1824 |
| Asn | Leu | Gln | His | Glu | His | Ile | Val | Lys | Phe | Tyr | Gly | Val | Cys | Val | Glu | |
| | | 595 | | | | | 600 | | | | | 605 | | | | |

| | | | | | | | | | | | | | | | | |
|---|---|---|---|---|---|---|---|---|---|---|---|---|---|---|---|---|
| GGC | GAC | CCA | CTC | ATC | ATG | GTC | TTT | GAG | TAC | ATG | AAG | CAC | GGG | GAC | CTC | 1872 |
| Gly | Asp | Pro | Leu | Ile | Met | Val | Phe | Glu | Tyr | Met | Lys | His | Gly | Asp | Leu | |
| | 610 | | | | 615 | | | | | 620 | | | | | | |
| AAC | AAG | TTC | CTT | AGG | GCA | CAC | GGG | CCC | GAC | GCA | GTG | CTG | ATG | GCA | GAG | 1920 |
| Asn | Lys | Phe | Leu | Arg | Ala | His | Gly | Pro | Asp | Ala | Val | Leu | Met | Ala | Glu | |
| 625 | | | | | 630 | | | | | 635 | | | | | 640 | |
| GGT | AAC | CCG | CCC | ACA | GAG | CTG | ACG | CAG | TCG | CAG | ATG | CTG | CAC | ATC | GCT | 1968 |
| Gly | Asn | Pro | Pro | Thr | Glu | Leu | Thr | Gln | Ser | Gln | Met | Leu | His | Ile | Ala | |
| | | | | 645 | | | | | 650 | | | | | 655 | | |
| CAG | CAA | ATC | GCA | GCA | GGT | ATG | GTC | TAC | CTG | GCG | TCC | CAA | CAC | TTT | GTG | 2016 |
| Gln | Gln | Ile | Ala | Ala | Gly | Met | Val | Tyr | Leu | Ala | Ser | Gln | His | Phe | Val | |
| | | | 660 | | | | 665 | | | | | 670 | | | | |
| CAC | CGT | GAC | CTG | GCC | ACC | CGG | AAC | TGC | CTG | GTG | GGA | GAG | AAC | CTG | CTG | 2064 |
| His | Arg | Asp | Leu | Ala | Thr | Arg | Asn | Cys | Leu | Val | Gly | Glu | Asn | Leu | Leu | |
| | | 675 | | | | 680 | | | | | 685 | | | | | |
| GTG | AAA | ATT | GGG | GAC | TTT | GGG | ATG | TCC | CGA | GAT | GTG | TAC | AGC | ACC | GAC | 2112 |
| Val | Lys | Ile | Gly | Asp | Phe | Gly | Met | Ser | Arg | Asp | Val | Tyr | Ser | Thr | Asp | |
| | 690 | | | | | 695 | | | | | 700 | | | | | |
| TAC | TAT | CGG | GTC | GGT | GGC | CAC | ACA | ATG | TTG | CCC | ATC | CGA | TGG | ATG | CCT | 2160 |
| Tyr | Tyr | Arg | Val | Gly | Gly | His | Thr | Met | Leu | Pro | Ile | Arg | Trp | Met | Pro | |
| 705 | | | | | 710 | | | | | 715 | | | | | 720 | |
| CCA | GAG | AGC | ATC | ATG | TAT | AGG | AAA | TTC | ACC | ACC | GAG | AGC | GAC | GTC | TGG | 2208 |
| Pro | Glu | Ser | Ile | Met | Tyr | Arg | Lys | Phe | Thr | Thr | Glu | Ser | Asp | Val | Trp | |
| | | | | 725 | | | | | 730 | | | | | 735 | | |
| AGC | CTG | GGC | GTT | GTG | TTG | TGG | GAG | ATC | TTC | ACC | TAC | GGC | AAG | CAG | CCC | 2256 |
| Ser | Leu | Gly | Val | Val | Leu | Trp | Glu | Ile | Phe | Thr | Tyr | Gly | Lys | Gln | Pro | |
| | | | 740 | | | | 745 | | | | | 750 | | | | |
| TGG | TAT | CAG | CTA | TCG | AAC | AAT | GAG | GTG | ATA | GAG | TGC | ATC | ACC | CAG | GGA | 2304 |
| Trp | Tyr | Gln | Leu | Ser | Asn | Asn | Glu | Val | Ile | Glu | Cys | Ile | Thr | Gln | Gly | |
| | | 755 | | | | 760 | | | | | 765 | | | | | |
| AGA | GTC | CTT | CAG | CGG | CCT | CGA | ACC | TGT | CCC | CAG | GAG | GTG | TAT | GAG | CTC | 2352 |
| Arg | Val | Leu | Gln | Arg | Pro | Arg | Thr | Cys | Pro | Gln | Glu | Val | Tyr | Glu | Leu | |
| | 770 | | | | | 775 | | | | | 780 | | | | | |
| ATG | CTC | GGA | TGC | TGG | CAG | CGG | GAA | CCA | CAC | ACC | CGG | AAG | AAC | ATC | AAG | 2400 |
| Met | Leu | Gly | Cys | Trp | Gln | Arg | Glu | Pro | His | Thr | Arg | Lys | Asn | Ile | Lys | |
| 785 | | | | | 790 | | | | | 795 | | | | | 800 | |
| AGC | ATC | CAC | ACC | CTC | CTT | CAG | AAC | TTG | GCC | AAG | GCA | TCT | CCC | GTC | TAC | 2448 |
| Ser | Ile | His | Thr | Leu | Leu | Gln | Asn | Leu | Ala | Lys | Ala | Ser | Pro | Val | Tyr | |
| | | | | 805 | | | | | 810 | | | | | 815 | | |
| CTG | GAT | ATC | CTA | GGC | | | | | | | | | | | | 2463 |
| Leu | Asp | Ile | Leu | Gly | | | | | | | | | | | | |
| | | | 820 | | | | | | | | | | | | | |

( 2 ) INFORMATION FOR SEQ ID NO:2:

( i ) SEQUENCE CHARACTERISTICS:
        ( A ) LENGTH: 821 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ser | Pro | Trp | Leu | Lys | Trp | His | Gly | Pro | Ala | Met | Ala | Arg | Leu | Trp |
| 1 | | | | 5 | | | | | 10 | | | | | 15 | |
| Gly | Leu | Cys | Leu | Leu | Val | Leu | Gly | Phe | Trp | Arg | Ala | Ser | Leu | Ala | Cys |
| | | | 20 | | | | | 25 | | | | | 30 | | |
| Pro | Thr | Ser | Cys | Lys | Cys | Ser | Ser | Ala | Arg | Ile | Trp | Cys | Thr | Glu | Pro |
| | | | 35 | | | | | 40 | | | | | 45 | | |
| Ser | Pro | Gly | Ile | Val | Ala | Phe | Pro | Arg | Leu | Glu | Pro | Asn | Ser | Val | Asp |
| | 50 | | | | | 55 | | | | | 60 | | | | |

```
Pro Glu Asn Ile Thr Glu Ile Leu Ile Ala Asn Gln Lys Arg Leu Glu
 65              70                  75                  80

Ile Ile Asn Glu Asp Asp Val Glu Ala Tyr Val Gly Leu Arg Asn Leu
                 85                  90                  95

Thr Ile Val Asp Ser Gly Leu Lys Phe Val Ala Tyr Lys Ala Phe Leu
            100                 105                 110

Lys Asn Ser Asn Leu Arg His Ile Asn Phe Thr Arg Asn Lys Leu Thr
            115                 120                 125

Ser Leu Ser Arg Arg His Phe Arg His Leu Asp Leu Ser Asp Leu Ile
            130                 135                 140

Leu Thr Gly Asn Pro Phe Thr Cys Ser Cys Asp Ile Met Trp Leu Lys
145                 150                 155                 160

Thr Leu Gln Glu Thr Lys Ser Ser Pro Asp Thr Gln Asp Leu Tyr Cys
                165                 170                 175

Leu Asn Glu Ser Ser Lys Asn Met Pro Leu Ala Asn Leu Gln Ile Pro
            180                 185                 190

Asn Cys Gly Leu Pro Ser Ala Arg Leu Ala Ala Pro Asn Leu Thr Val
            195                 200                 205

Glu Glu Gly Lys Ser Val Thr Leu Ser Cys Ser Val Gly Gly Asp Pro
210                 215                 220

Leu Pro Thr Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
    290                 295                 300

Phe Thr Val Arg Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
            325                 330                 335

Thr Asn His Thr Glu Tyr His Gly Cys Leu Gln Leu Asp Asn Pro Thr
            340                 345                 350

His Met Asn Asn Gly Asp Tyr Thr Leu Met Ala Lys Asn Glu Tyr Gly
            355                 360                 365

Lys Asp Glu Arg Gln Ile Ser Ala His Phe Met Gly Arg Pro Gly Val
    370                 375                 380

Asp Tyr Glu Thr Asn Pro Asn Tyr Pro Glu Val Leu Tyr Glu Asp Trp
385                 390                 395                 400

Thr Thr Pro Thr Asp Ile Gly Asp Thr Thr Asn Lys Ser Asn Glu Ile
            405                 410                 415

Pro Ser Thr Asp Val Ala Asp Gln Ser Asn Arg Glu His Leu Ser Val
            420                 425                 430

Tyr Ala Val Val Val Ile Ala Ser Val Val Gly Phe Cys Leu Leu Val
        435                 440                 445

Met Leu Leu Leu Leu Lys Leu Ala Arg His Ser Lys Phe Gly Met Lys
    450                 455                 460

Gly Pro Ala Ser Val Ile Ser Asn Asp Asp Asp Ser Ala Ser Pro Leu
465                 470                 475                 480

His His Ile Ser Asn Gly Ser Asn Thr Pro Ser Ser Ser Glu Gly Gly
```

|     |     |     |     | 485 |     |     |     | 490 |     |     |     | 495 |     |     |
| --- | --- | --- | --- | --- | --- | --- | --- | --- | --- | --- | --- | --- | --- | --- |
| Pro | Asp | Ala | Val<br>500 | Ile | Ile | Gly | Met | Thr<br>505 | Lys | Ile | Pro | Val | Ile<br>510 | Glu | Asn |
| Pro | Gln | Tyr<br>515 | Phe | Gly | Ile | Thr | Asn<br>520 | Ser | Gln | Leu | Lys | Pro<br>525 | Asp | Thr | Phe |
| Val | Gln<br>530 | His | Ile | Lys | Arg | His<br>535 | Asn | Ile | Val | Leu | Lys<br>540 | Arg | Glu | Leu | Gly |
| Glu<br>545 | Gly | Ala | Phe | Gly | Lys<br>550 | Val | Phe | Leu | Ala | Glu<br>555 | Cys | Tyr | Asn | Leu | Cys<br>560 |
| Pro | Glu | Gln | Asp | Lys<br>565 | Ile | Leu | Val | Ala | Val<br>570 | Lys | Thr | Leu | Lys | Asp<br>575 | Ala |
| Ser | Asp | Asn | Ala<br>580 | Arg | Lys | Asp | Phe | His<br>585 | Arg | Glu | Ala | Glu | Leu<br>590 | Leu | Thr |
| Asn | Leu | Gln<br>595 | His | Glu | His | Ile | Val<br>600 | Lys | Phe | Tyr | Gly | Val<br>605 | Cys | Val | Glu |
| Gly | Asp<br>610 | Pro | Leu | Ile | Met | Val<br>615 | Phe | Glu | Tyr | Met | Lys<br>620 | His | Gly | Asp | Leu |
| Asn<br>625 | Lys | Phe | Leu | Arg | Ala<br>630 | His | Gly | Pro | Asp | Ala<br>635 | Val | Leu | Met | Ala | Glu<br>640 |
| Gly | Asn | Pro | Pro | Thr<br>645 | Glu | Leu | Thr | Gln | Ser<br>650 | Gln | Met | Leu | His | Ile<br>655 | Ala |
| Gln | Gln | Ile | Ala<br>660 | Ala | Gly | Met | Val | Tyr<br>665 | Leu | Ala | Ser | Gln | His<br>670 | Phe | Val |
| His | Arg | Asp<br>675 | Leu | Ala | Thr | Arg | Asn<br>680 | Cys | Leu | Val | Gly | Glu<br>685 | Asn | Leu | Leu |
| Val | Lys<br>690 | Ile | Gly | Asp | Phe | Gly<br>695 | Met | Ser | Arg | Asp | Val<br>700 | Tyr | Ser | Thr | Asp |
| Tyr<br>705 | Tyr | Arg | Val | Gly | Gly<br>710 | His | Thr | Met | Leu | Pro<br>715 | Ile | Arg | Trp | Met | Pro<br>720 |
| Pro | Glu | Ser | Ile | Met<br>725 | Tyr | Arg | Lys | Phe | Thr<br>730 | Thr | Glu | Ser | Asp | Val<br>735 | Trp |
| Ser | Leu | Gly | Val<br>740 | Val | Leu | Trp | Glu | Ile<br>745 | Phe | Thr | Tyr | Gly | Lys<br>750 | Gln | Pro |
| Trp | Tyr | Gln<br>755 | Leu | Ser | Asn | Asn | Glu<br>760 | Val | Ile | Glu | Cys | Ile<br>765 | Thr | Gln | Gly |
| Arg | Val<br>770 | Leu | Gln | Arg | Pro | Arg<br>775 | Thr | Cys | Pro | Gln | Glu<br>780 | Val | Tyr | Glu | Leu |
| Met<br>785 | Leu | Gly | Cys | Trp | Gln<br>790 | Arg | Glu | Pro | His | Thr<br>795 | Arg | Lys | Asn | Ile | Lys<br>800 |
| Ser | Ile | His | Thr | Leu<br>805 | Leu | Gln | Asn | Leu | Ala<br>810 | Lys | Ala | Ser | Pro | Val<br>815 | Tyr |
| Leu | Asp | Ile | Leu<br>820 | Gly |     |     |     |     |     |     |     |     |     |     |     |

What is claimed is:

1. A PC12 cell line transformed with a nucleic acid sequence encoding a trkB receptor protein wherein said nucleic acid sequence is expressed.